United States Patent

Takagi et al.

(10) Patent No.: US 9,414,808 B2
(45) Date of Patent: Aug. 16, 2016

(54) ULTRASOUND DIAGNOSTIC DEVICE, ULTRASOUND DIAGNOSTIC METHOD, AND RECORDING MEDIUM STORING NON-TRANSITORY COMPUTER-READABLE PROGRAM

(71) Applicant: Konica Minolta, Inc., Tokyo (JP)

(72) Inventors: Kazuya Takagi, Toyonaka (JP); Yuki Matsumoto, Settsu (JP)

(73) Assignee: KONICA MINOLTA, INC., Tokyo (JP)

( * ) Notice: Subject to any disclaimer, the term of this patent is extended or adjusted under 35 U.S.C. 154(b) by 178 days.

(21) Appl. No.: 14/463,020

(22) Filed: Aug. 19, 2014

(65) Prior Publication Data

US 2015/0057545 A1    Feb. 26, 2015

(30) Foreign Application Priority Data

Aug. 21, 2013   (JP) ................... 2013-171037
Aug. 13, 2014   (JP) ................... 2014-164672

(51) Int. Cl.
*A61B 8/14*       (2006.01)
*A61B 8/00*       (2006.01)
*G06T 7/00*       (2006.01)
*A61B 8/08*       (2006.01)

(52) U.S. Cl.
CPC ............. *A61B 8/4254* (2013.01); *A61B 8/0875* (2013.01); *A61B 8/4209* (2013.01); *A61B 8/5223* (2013.01); *G06T 7/0012* (2013.01); *A61B 8/4405* (2013.01); *A61B 8/486* (2013.01); *A61B 8/488* (2013.01); *A61B 8/5215* (2013.01); *G06T 2207/10132* (2013.01); *G06T 2207/30008* (2013.01)

(58) Field of Classification Search
CPC ...... A61B 8/06; A61B 8/0858; A61B 8/0875; A61B 8/14; A61B 8/463; A61B 8/5223; G06T 2207/10132; G06T 2207/30008; G06T 7/0083
See application file for complete search history.

(56) References Cited

U.S. PATENT DOCUMENTS

2013/0060121 A1    3/2013  Patwardhan et al.

FOREIGN PATENT DOCUMENTS

JP    2011-072522 A    4/2011
JP    2013-056156 A    3/2013

OTHER PUBLICATIONS

Koike T.; The new concept of rheumatoid arthritis care—ultrasonography for joints; Medical Review Co., Ltd.; Mar. 2010; pp. 40-43.

*Primary Examiner* — Mark Remaly
(74) *Attorney, Agent, or Firm* — Lucas & Mercanti, LLP

(57) ABSTRACT

An ultrasound diagnostic device 101 is equipped with a probe distance determiner 7 and a screen creator 8. The probe distance determiner 7 analyses a positional relationship between a probe and an area subject to measurement appearing in an ultrasound image, and determines whether or not the analysed positional relationship is appropriate. The screen creator 8 notifies a user of determination results. An appropriate positional relationship is one in which a pixel region having luminance characteristics of a gelatinous medium is present between an element array of an ultrasound probe 102 and the area subject to measurement appearing in the ultrasound image, and in which the distance between the prove and the area subject to measurement exceeds a predetermined threshold across the entire length of the element array.

13 Claims, 23 Drawing Sheets

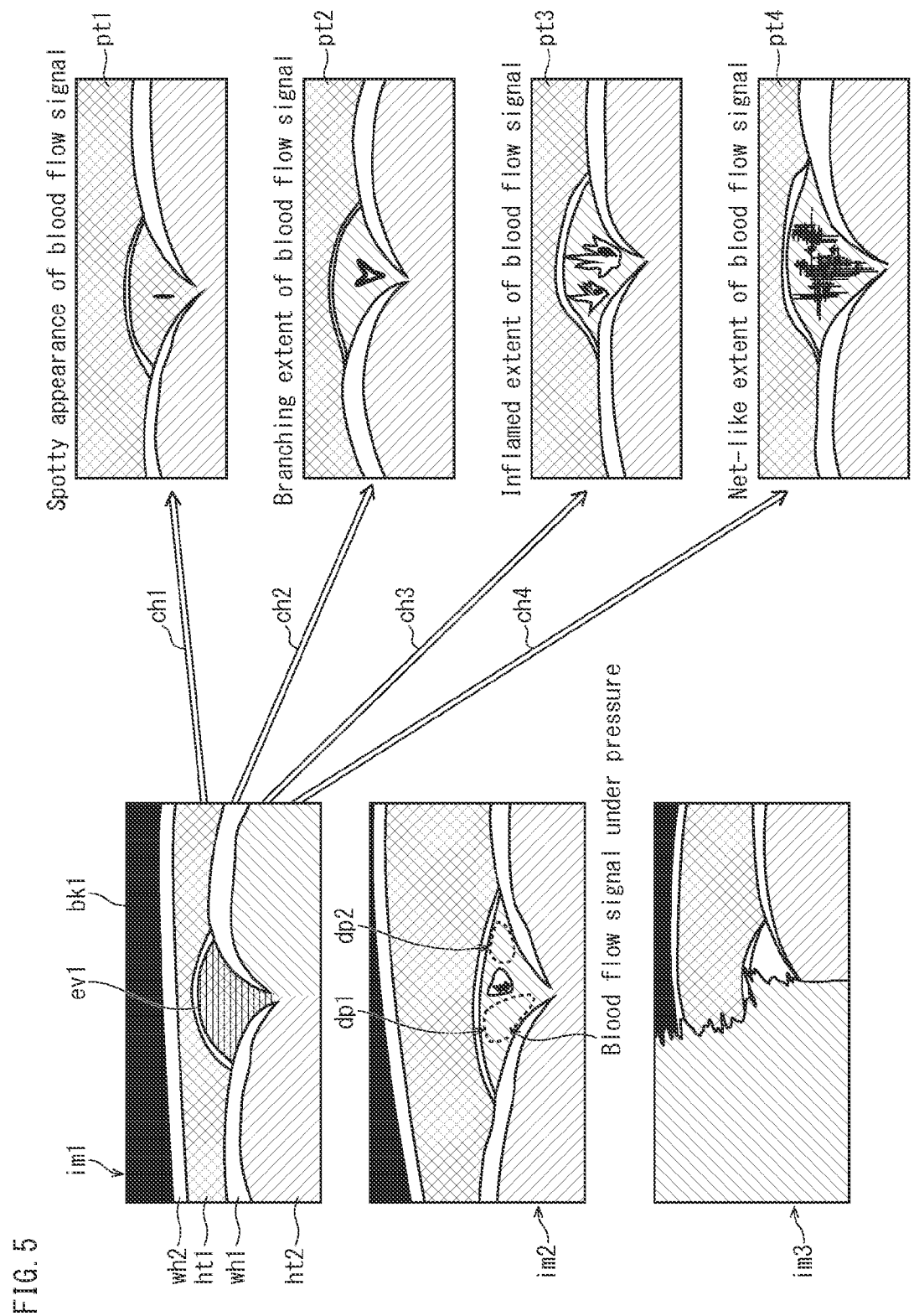

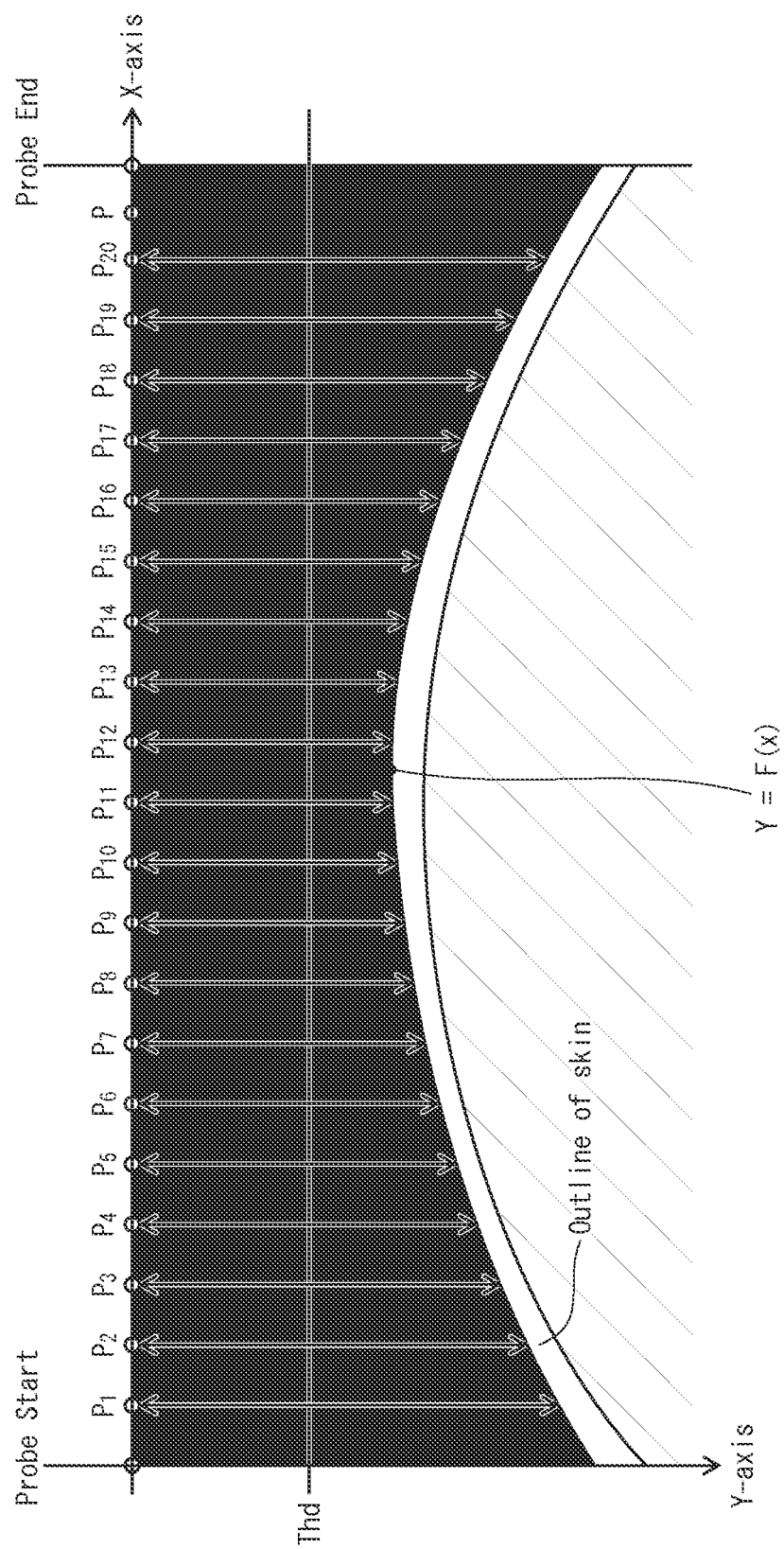

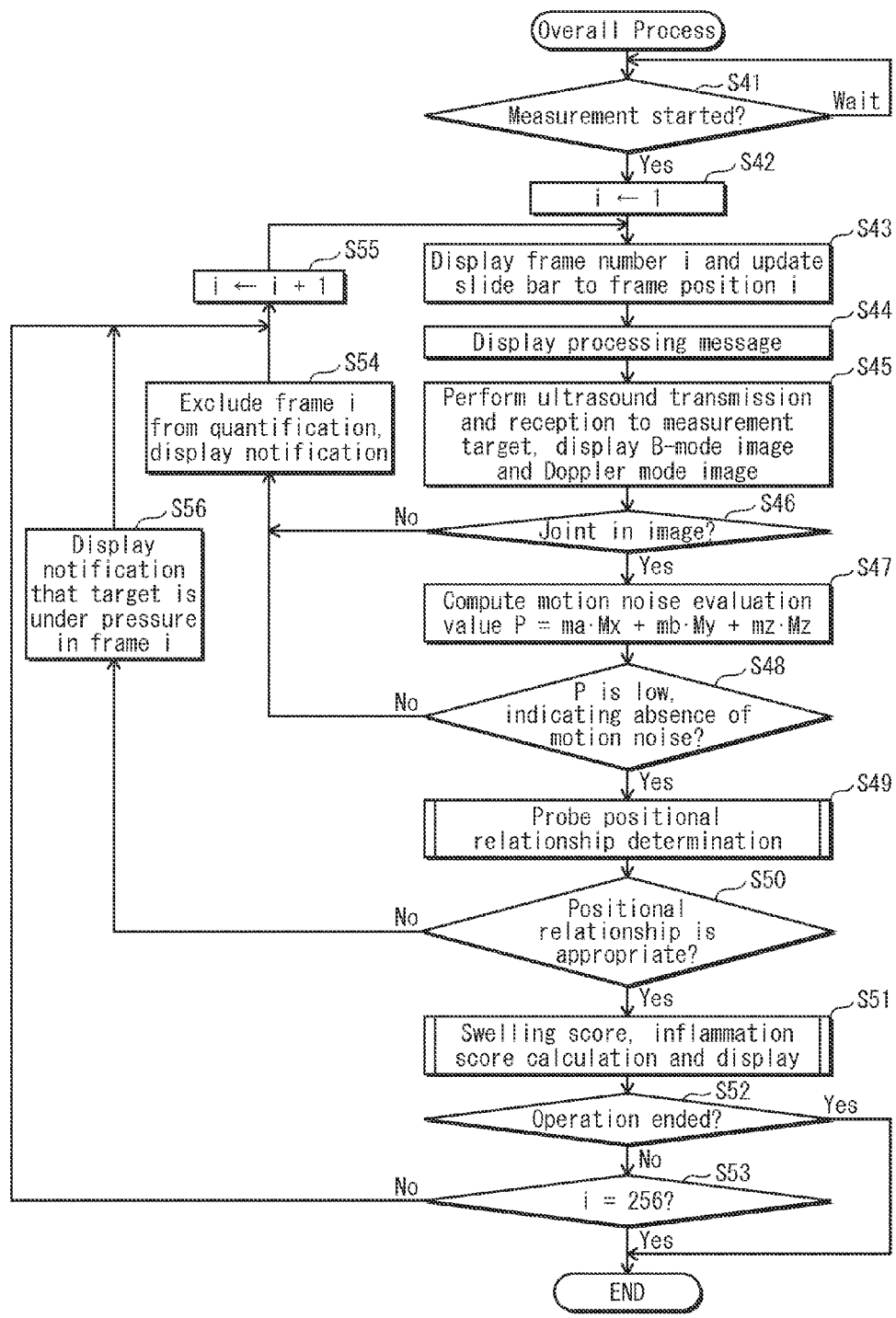

ULTRASOUND DIAGNOSTIC DEVICE, ULTRASOUND DIAGNOSTIC METHOD, AND RECORDING MEDIUM STORING NON-TRANSITORY COMPUTER-READABLE PROGRAM

CROSS REFERENCE TO RELATED APPLICATION

This Application claims the priority of Japanese Patent Application No. 2013-171037 filed on Aug. 21, 2013 and Japanese Patent Application No. 2014-164672 filed on Aug. 13, 2014, both applications are incorporated by reference herein.

BACKGROUND OF THE INVENTION (1) Field of the Invention

The present invention relates to the technological field of ultrasound diagnostic devices.

(2) Description of the Related Art

Ultrasound diagnostic is a diagnostic method that involves applying an ultrasound probe to the body surface of a subject in order to obtain an image from within the subject's body. This method has long been used for diagnostic and observation of the heart, abdomen, uterus, and so on. In recent years, improved resolution of ultrasound diagnostic device has enabled observation of areas closer to the body surface. This has lead to ultrasound diagnostic devices being used in orthopaedic areas for observation of bone, tendon, muscle, and so on. Ultrasound diagnostic devices are also used for evaluation of inflammation in joints for rheumatism diagnostics.

SUMMARY OF THE INVENTION

Problem to be Solved by the Invention

For instance, when imaging a large blood vessel such as the carotid artery, pressure applied by the probe does not produce a change in the shape of the area subject to measurement. However, when evaluating inflammation in a joint, the area subject to measurement is new blood vessels forming in a finger articular capsule. Thus, a slight deformation of the new blood vessels produced when the probe is applied to the body may have a large effect on diagnostic results.

Measuring the probe pressure by providing a sensor on the probe or on the body has been considered. However, given the small contact surface area between the probe and the finger joint, a precise measurement of pressure by the probe in that area is difficult to achieve.

Means for Solving the Problem

The present disclosure aims to provide an ultrasound diagnostic device promoting appropriate probe technique when the internal structure of the area subject to measurement is delicate and susceptible to changes due to pressure from probe contact.

In order to achieve the aim, an ultrasound diagnostic device, comprising: a transceiver circuit causing an ultrasound probe to transmit and receive an ultrasound; an image generation circuit generating an ultrasound image according to the ultrasound received by the ultrasound probe; and a control circuit, wherein the ultrasound image is a cross-section that includes a measurement target, and the control circuit executes: a region determination of determining one of a presence and a thickness of a pixel region having a luminance distribution specific to gelatinous material, within a portion of the ultrasound image opposite an element array of the ultrasound probe; and a positional relationship notification of making a notification to a user regarding whether or not there is an appropriate positional relationship between the measurement target and the ultrasound probe, according to the one of the presence and the thickness of the pixel region.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIG. 5 illustrates examples of a Doppler mode image on a display 103 in situations illustrated by FIGS. 4A-4C;

FIG. 7 illustrates continuous length measurement of low-luminance pixels;

FIG. 22 illustrates an example of overall processing by the ultrasound diagnostic device pertaining to Embodiment 2.

DESCRIPTION OF THE PREFERRED EMBODIMENT

Figure 1:
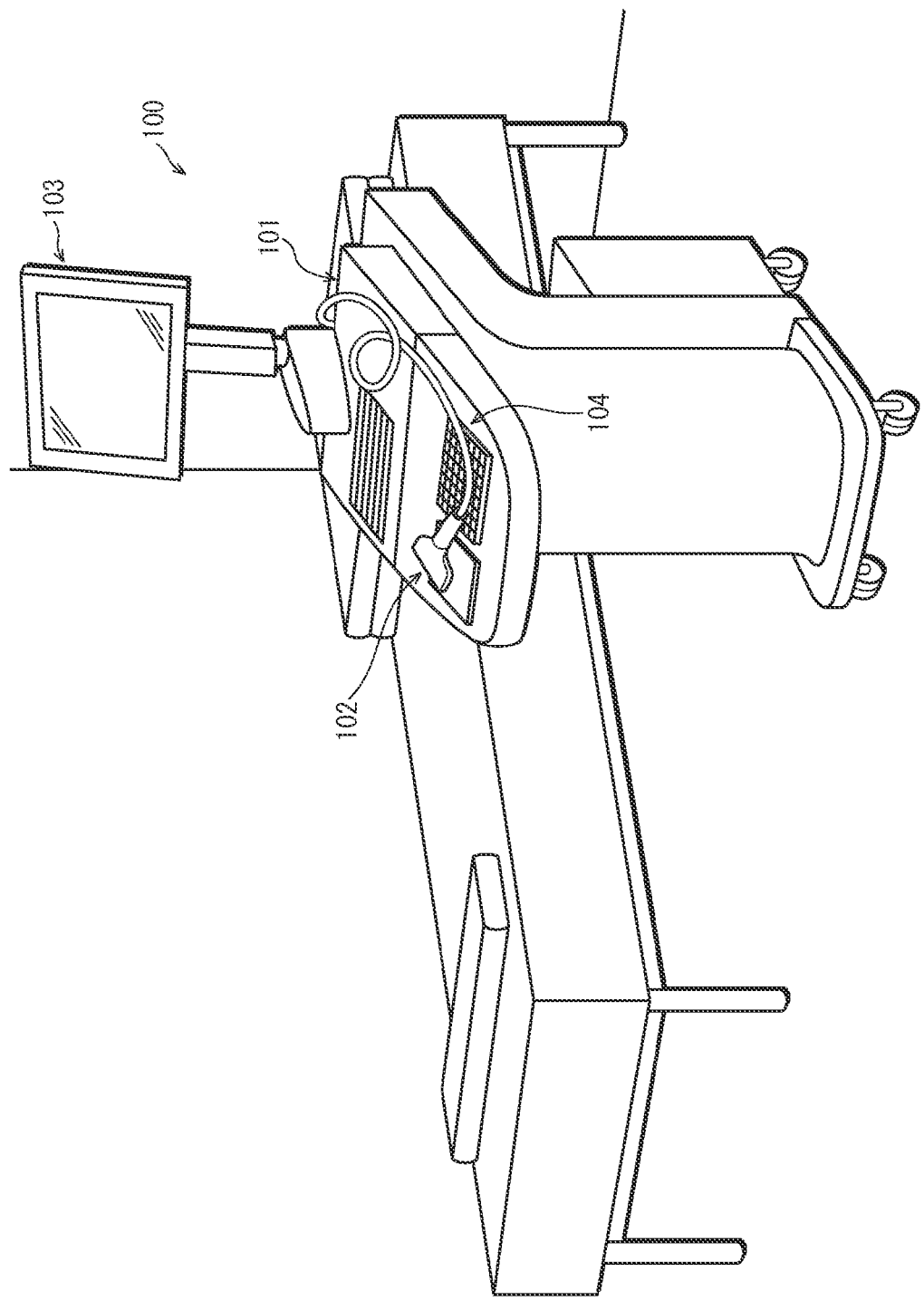
FIG. 1 is a perspective view diagram of an ultrasound diagnostic system.

The inventors faced the following technical challenge in realising a joint inflammation evaluation using an ultrasound diagnostic device.

The ultrasound operation made for a joint inflammation subject is performed by making an image of unusual blood flow occurring within the articular cavity. Specifically, unusual blood flow occurring in the articular cavity is made visible by creating a Doppler mode image by a probe passing ultrasound therethrough. The surface area occupied by blood flow in the Doppler mode image so acquired is then evaluated. The evaluation method for the blood flow surface area may be a four-step semi-quantification evaluation method, an eight-step semi-quantification method, or a quantification evaluation method. The four-step semi-quantification evaluation involves evaluating a blood flow signal in an area outlined by the articular capsule and bone cortex as one of four steps A-D, namely A: No blood flow signal, B: Single blood flow signal present, C: 50% blood flow signals or less, and D: Over 50% blood flow signals (see also Non-Patent Literature, The New Concept of Rheumatoid Arthritis Care—Ultrasonography for Joints—p. 40-43).

The eight-step semi-quantification evaluation involves categorising an unusual blood flow signal discovered in the articular cavity as one of eight grades (i.e., No blood flow, Grade I+: spotty blood flow, Grade II+: branching blood flow, Grade II++: Advanced branching blood flow, Grade III+: inflamed blood flow, Grade III++: Advanced inflamed blood flow, Grade IV+: Net-like blood flow, and Grade IV++: Advanced net-like blood flow).

The quantification evaluation method involves preparing a region of interest (hereinafter, ROI), that is rectangular and centred on a portion where unusual blood flow is concentrated, and calculating an absolute pixel value within the ROI.

The operator is able to perform the four-step semi-quantification evaluation method, the eight-step semi-quantification method, or the quantification evaluation method using the B-mode image and the Doppler mode image, However, the four-step semi-quantification evaluation method and the eight-step semi-quantification method are performed subjectively by the operator. Also, these methods require some time given that there are several joints to evaluate. In addition, operator subjectivity produces different results among operators. In order to resolve these problems, methods have been proposed for calculating an objective (i.e., quantified) degree of inflammation. For example, Patent Literature 1 (Japanese Patent Application Publication No. 2013-056156) proposes a method of quantifying a degree of inflammation by cutting out an articular capsule area specified on a bone surface, and analysing the articular capsule area.

However, although this evaluation method is reliable, the influence of the ultrasound probe on the blood flow signal at the area subject to measurement is not taken into consideration. This influence is pressure applied by the ultrasound probe preventing certain elements from appearing in the Doppler mode image. Specifically, the articular cavity is soft and as such, pressure from applying to probe to the joint causes flow speed in some of the new blood vessels to change when said new blood vessels are branching or inflamed. When this change in flow speed causes blood flow signal of the new blood vessels to be lost from the Doppler mode image, the results of the four-step semi-quantification evaluation method, the eight-step semi-quantification method, and the quantification evaluation method are affected.

Specifically, when a result of Grade III+ or III++ should be produced for new blood vessels spreading inflammation, the pressure applied to the articular cavity may cause the new blood vessels to appear spotty or branching, producing an evaluation result of Grade I+ or II+.

As such, it is recommended that the probe be held above the body surface. For example, Patent Literature 2 (Japanese Patent Application Publication No. 2011-72522) proposes a method of evaluating pressure applied by an ultrasound probe according distance from bone to body surface in a reference frame, and distance from bone to body surface in a current frame.

Specifically, Patent Literature calculates the pressure applied by the probe by calculating a pressure $\alpha(=(L1-L2)/L1)$ as indicated in Math. 1 (see paragraph 0043). Here, L1 is the distance from the body surface to a bone region without pressure, and L2 is the distance from the bone region to the body surface. A determination is made regarding whether or not the result $\alpha$ of calculating $(L1-L2)/L1$ exceeds a threshold. In the affirmative case, the colour of a bar is changed (see paragraph 0046). However, the new blood vessels in the articular cavity of the finger are especially delicate, such that deformation in the vascular cross-section may occur even though there may be no change in the distance from the bone region to the body surface, which produces nearly zero pressure in the above-described method. No method for accurate measurement of such a delicate diagnostic subject has been established in the field of ultrasound diagnostic methods.

This technical obstacle has been overcome by an ultrasound diagnostic device, comprising: a transceiver circuit causing an ultrasound probe to transmit and receive an ultrasound; an image generation circuit generating an ultrasound image according to the ultrasound received by the ultrasound probe; and a control circuit, wherein the ultrasound image is a cross-section that includes a measurement target, and the control circuit executes: a region determination of determining one of a presence and a thickness of a pixel region having a luminance distribution specific to gelatinous material, within a portion of the ultrasound image opposite an element array of the ultrasound probe; and a positional relationship notification of making a notification to a user regarding whether or not there is an appropriate positional relationship between the measurement target and the ultrasound probe, according to the one of the presence and the thickness of the pixel region.

Making the notification regarding whether or not the positional relationship between the measurement target and the ultrasound probe, as determined according to presence of the gelatinous material, is appropriate enables a user to accurately capture the shape of a delicate diagnostic target by following the notification.

The user receives guidance for an appropriate probe position such that no pressure from the probe is detected by a sensor.

(Embodiment 1)

Embodiment 1 seeks to achieve improved operation during ultrasound scanning performed by a user using an ultrasound probe 102, through real-time analysis of whether or not there is an appropriate positional relationship between the ultrasound probe 102 and a body surface, and making a display on the ultrasound probe 102 when the positional relationship is not appropriate. That is, the ultrasound diagnostic device of Embodiment 1 differs from a known ultrasound diagnostic device in being configured, as described above, to make a determination regarding a positional relationship of the ultrasound probe 102 based on an ultrasound image, and to make a notification of the positional relationship.

(Usage Environment of Ultrasound Diagnostic Device)

The usage environment for the ultrasound diagnostic device of the present Embodiment is described below. The ultrasound diagnostic device is used in a diagnostic system at a medical facility. FIG. 1 is a perspective view diagram of an ultrasound diagnostic system that includes the ultrasound diagnostic device. As shown, the ultrasound diagnostic system 100 includes the ultrasound diagnostic device 101, the ultrasound probe 102, a display 103, and an external input 104. In FIG. 1, the ultrasound probe 102, the display 103, and the external input 104 are independent components from the ultrasound diagnostic device 101.

The ultrasound diagnostic device 101 serves the central role in the ultrasound diagnostic system (as a hub device), receiving an output signal from the ultrasound probe 102 and an output signal from the external input 104, performing a diagnostic process, and displaying process results on the display 103.

The ultrasound probe 102 emits a transmit wave using an array of acoustic elements. The emitted wave is an ultrasound wave with portions that vary in acoustic impedance and that is reflected in accordance with these differences in acoustic impedance. The ultrasound probe 102 is applied to the body surface through a gel, such that the body surface and bones cause the reflection. The gel is a gelatinous medium serving to guide the ultrasound emitted by the ultrasound probe to the body, without loss. The reflected ultrasound is then received by the ultrasound probe 102.

The display 103 is a liquid crystal display (hereinafter, LCD) or the like displaying a B-mode image, a Doppler mode image, or the like generated from a reflected ultrasound signal, and displaying an indication of whether or not the positional relationship of the ultrasound probe 102 is appropriate.

The external input 104 is a keyboard, trackball, touch panel, or similar, enabling an operator to perform device operations.

(Usage by User)

Figure 2:
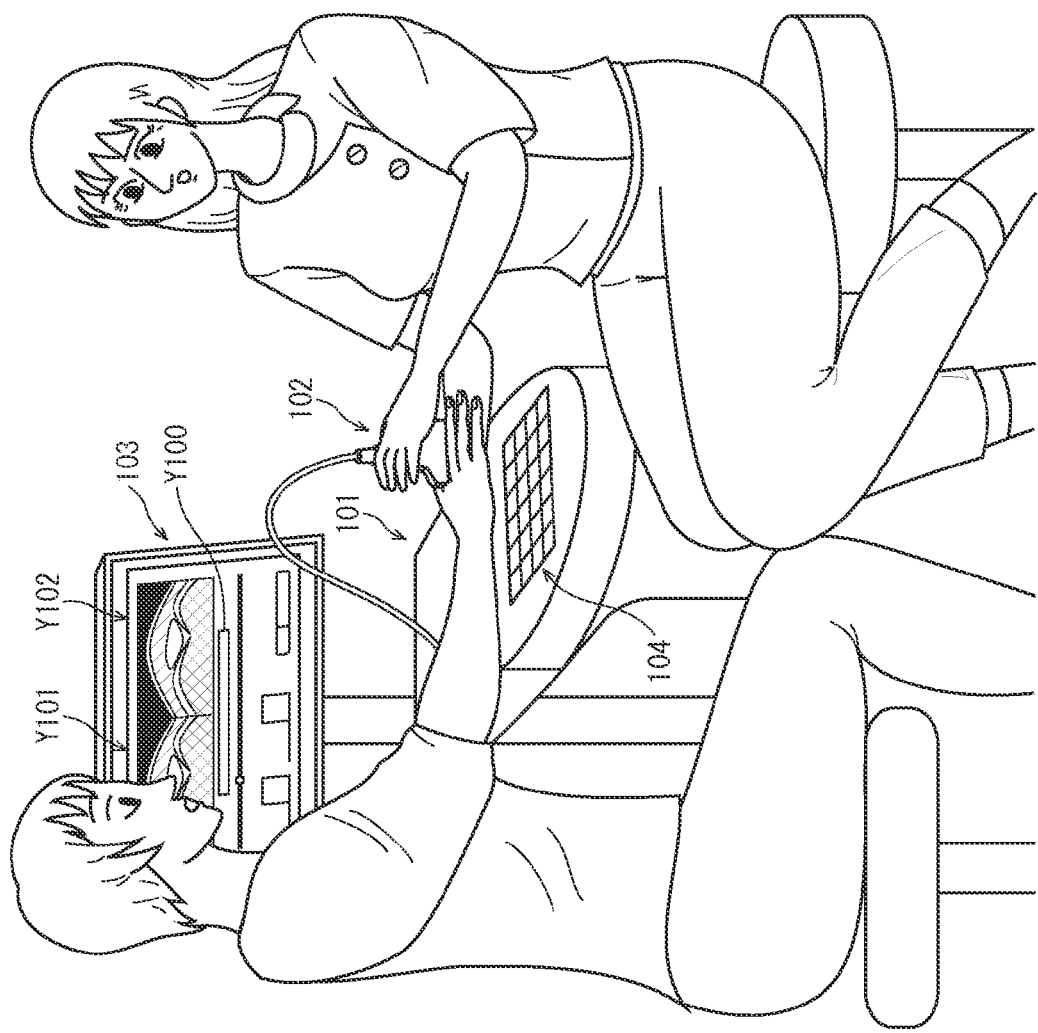
FIG. 2 illustrates the ultrasound diagnostic device 101 and an ultrasound probe 102 while in use.

The following describes a usage case illustrating how a user uses the ultrasound diagnostic device 101 and the ultrasound probe 102. FIG. 2 illustrates the ultrasound diagnostic device 101 and the ultrasound probe 102 while in use. As shown, a subject extends fingers while a doctor or clinical examiner on the right-hand side applies the ultrasound probe 102 to the fingers to view an ultrasound image thereof. Here, the display 103 displays a B-mode image Y 101, a Doppler mode image Y 102, and an indicator Y 100 indicating the positional relationship of the ultrasound probe 102. The display 103 displaying the indicator Y 100 enables the operator to check whether or not the ultrasound probe 102 is being applied correctly by looking at the display 103. When the positional relationship of the ultrasound probe 102 is not appropriate, an adjustment thereto can be performed while watching the indicator of display 103.

(Diagnostic Method Using Ultrasound Diagnostic Device)

Figure 3A:
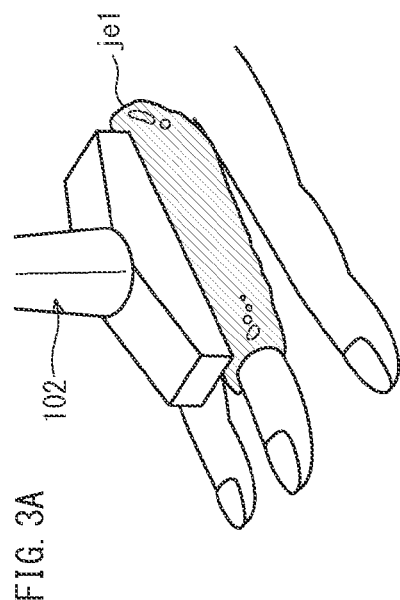
FIG. 3A illustrates gel applied to a finger joint surface that is a target for sending and receiving ultrasound and the ultrasound probe 102 applied longitudinally.
Figure 3B:
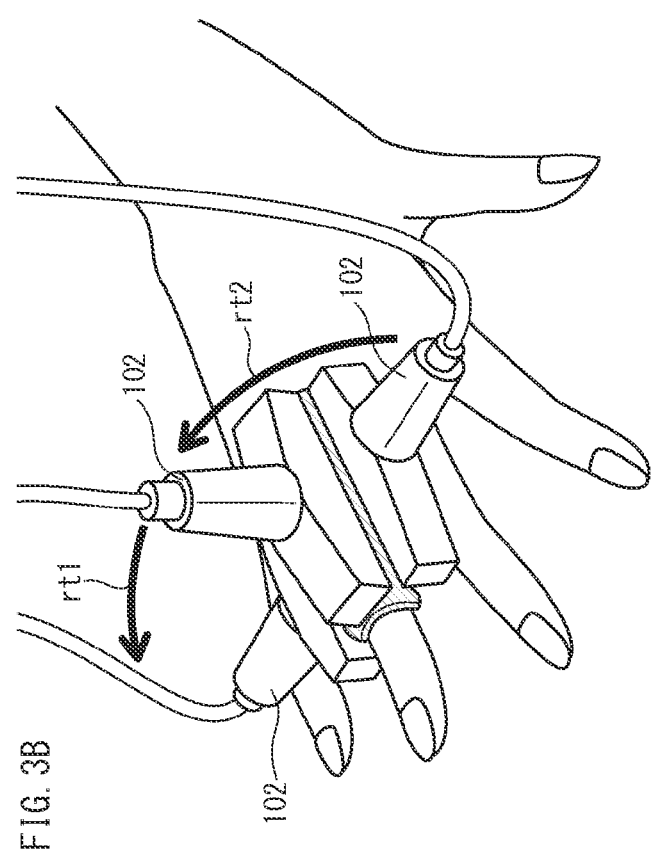
FIG. 3B illustrates the position of the ultrasound probe 102 changing over a 360° range around the joint.

The diagnostic method using the ultrasound diagnostic device is described below. FIGS. 3A and 3B illustrate a technique performed by the operator. The technique involves applying gel to the finger joint that is the subject of sending and receiving the ultrasound, and having the ultrasound probe 102 transmit and send the ultrasound in a longitudinal direction (FIG. 3A) and in a circumferential direction around 360° of the joint (FIG. 3B).

A gel layer, labelled jel in FIG. 3A, is formed around the finger joint through application. The ultrasound probe 102 is pressed against the gel layer.

FIG. 3B indicates displacement routes rt1 and rt2 for the ultrasound probe 102. As indicated, the ultrasound is transmitted and received around 360° of the finger joint at various orientations. The B-mode image Y 101 and the Doppler mode image Y 102 are cross-sections obtained at each position of transmission and reception, displayed on the display 103. Transmission and reception around the joint generates a plurality of ultrasound images. The ultrasound images include B-mode images and Doppler mode images. The Doppler mode images are images in which colour-change pixels (i.e., blood flow signal pixels) corresponding to blood flow speed in a measurement area are overlaid on the B-mode image. The ultrasound images thus generated are termed a frame image sequence. Within the frame image sequence, individual ultrasound images are termed frame images, and indicated by a frame number xx/256. New blood vessels in the articular cavity are fine details that cannot be accurately captured by the B-mode image. A Doppler window is thus set up for the articular cavity to create a Doppler mode image. The Doppler mode image is represented as pixels coloured according to blood flow speed at a position where the Doppler window is set up, thus revealing the presence of fine blood vessels and the extent thereof in the space.

(Positional Relationship of Ultrasound Probe)

Figure 4A:
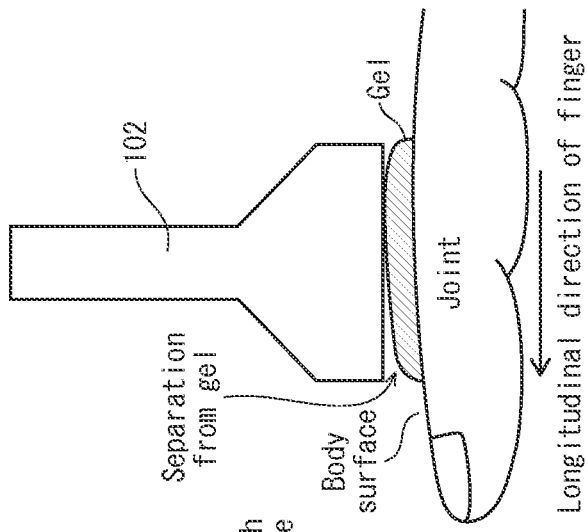
FIG. 4A illustrates the ultrasound probe 102 at a fixed separation from the gel.
Figure 4B:
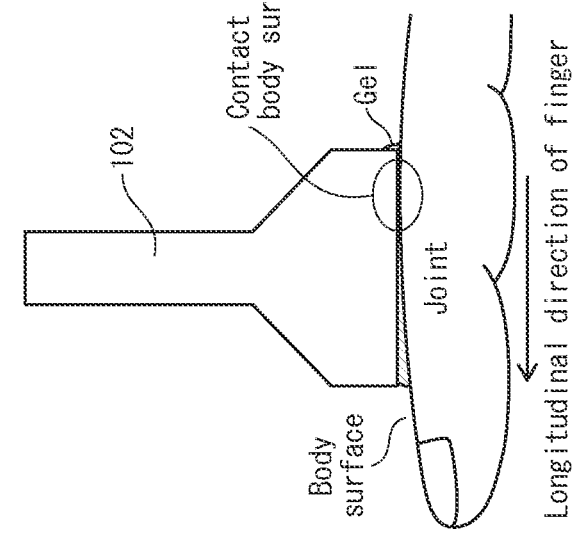
FIG. 4B illustrates some or all of the ultrasound probe 102 being in contact with the body surface despite the gel being present between the ultrasound probe 102 and the body surface.
Figure 4C:
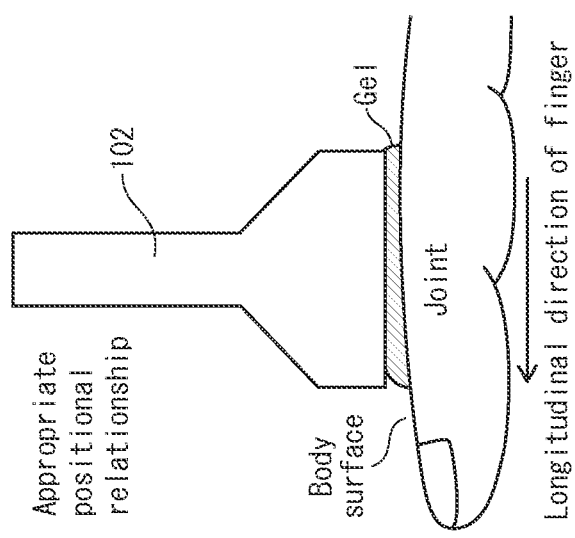
FIG. 4C illustrates a gap between the ultrasound probe 102 and the gel.

FIGS. 4A-4C show the positional relationship of the ultrasound probe 102 when transmitting and receiving the ultrasound. FIG. 4A illustrates a case where the ultrasound probe is at a fixed separation through the gel. FIG. 4B illustrates a case where, despite the gel being present between the ultrasound probe 102 and the body surface, some or all of the ultrasound probe 102 is in contact with the body surface. FIG. 4C illustrates a case where a gap is present between the ultrasound probe 102 and the gel. When the positional relationship of the ultrasound probe 102 is as shown in any of FIGS. 4A-4C, the Doppler mode image shown on the display 103 is as shown in FIG. 5. In FIG. 5, image im1 represents a Doppler mode image displayed when the positional relationship of the ultrasound probe 102 is as shown in FIG. 4A. Here, white regions wh1 and wh2 represent high-luminance regions. Also, black region bk1 represents a low-luminance pixel region made up of pixels having a uniformly low luminance. The low luminance may refer to pixels having a value below a threshold, as well as to pixels having a luminance of zero. Hatched regions ht1 and ht2 represent areas having a luminance gradient (i.e., luminance gradient regions). The following describes the body tissue represented by each of these regions in the ultrasound image.

The white regions wh1 and wh2 represent skin and bone. Skin and bone are comparatively solid tissues and thus appear to have high luminance in the ultrasound image. Most of the ultrasound is reflected by the bone surface, such that the interior of the bone is not depicted. Only areas corresponding to bone cortex on the bone surface appear depicted as high-luminance regions.

The luminance gradient region ht1 represents muscle fibre. The luminance of the articular capsule is relatively low, in comparison to the pixels depicting bone and skin. The articular cavity is located within the articular capsule. The black region bk1 represents the gel. The gel is transmissive to ultrasound and thus has no hue.

Ultrasound image im1 in FIG. 5 depicts a gel layer with sufficient thickness. The gel layer serves as a cushion maintaining an appropriate positional relationship between the ultrasound probe 102 and the area subject to measurement. When the positional relationship between the ultrasound probe 102 and the area subject to measurement is appropriate, a blood flow signal corresponding to the subject's symptoms appears in the articular cavity. The occurrence of new blood vessels in the articular cavity is described below. The articular cavity is formed where the bone cortex is covered by the articular capsule. In a healthy subject, the articular cavity is filled with liquid. However, as rheumatism symptoms progress, new blood vessels form within the articular cavity. Early symptoms involve spotty new blood vessels. As symptoms progress, the new blood vessels extend into branches and eventually fill the articular cavity and become inflammation. In the final stages, the articular cavity is completely filled with new blood vessels in a net-like structure.

The right-hand side of FIG. 5 illustrates these stages. The arrows ch1, ch2, ch3, and ch4 represent the changing blood flow signal at each stage. Image pt1 shows a blood flow signal in which the spotty vessels appear. Image pt2 shows a blood flow signal in which the branch-like vessels appear. Image pt3 shows a blood flow signal in which the inflamed vessels appear. Image pt3 shows a blood flow signal in which the net-like vessels appear.

The positional relationship depicted in each of FIGS. 4A-4C and the ultrasound images of FIG. 5 are summarised as follows. When the positional relationship between the ultrasound probe 102 and the body surface is appropriate as shown in FIG. 4A, then the ultrasound probe 102 is elevated slightly above the body surface rather than being in direct contact, with the gel layer filling the entire space between the ultrasound probe and the body surface. Detecting the presence of a Doppler signal in such conditions produces a normal blood flow signal depicting one of ultrasound images pt1-pt4 from which measurement can be performed. The blood flow signal enables evaluation of a degree of inflammation.

When the ultrasound probe 102 presses the body surface on one side as shown in FIG. 4b, then the ultrasound probe is direct contact with the body surface. In FIG. 4B, the gel layer is not thick enough on the right-hand side of the image, such that the gel layer is unable to serve as a cushion. In such conditions, the contact of the ultrasound probe 102 applies pressure to the new blood vessels near the body surface. Thus, as depicted in ultrasound image im2 of FIG. 5, partial loss of the signal (see portions dp1 and dp2) occurs. Such a blood flow signal is not usable for accurate evaluation of inflammation. When the ultrasound probe 102 is too far from the body surface as shown in FIG. 4C, the ultrasound probe 102 is elevated slightly above the body surface rather than being in direct contact, but the space between the ultrasound probe 102 and the body surface is not completely filled by the gel layer. In portions not filled by the gel layer, the ultrasound from the ultrasound probe 102 is reflected by the probe surface and does not reach either the gel or the body. Thus, as depicted in ultrasound image im3 of FIG. 5, half of the ultrasound image is missing and cannot be used to correctly evaluate the degree of inflammation. In the present Embodiment, the gel layer serves as a cushion with respect to the body surface. Thus, a determination is made regarding whether or not the gel layer is present in the ultrasound images (i.e., the B-mode image and the Doppler mode image) at a portion facing the acoustic element array of the ultrasound probe 102.

In the present Embodiment, the acoustic element array direction of the ultrasound probe 102 matches the longitudinal direction of the ultrasound image. In such a case, the portion opposite the acoustic element array is a region located somewhat deeper than the surface of the ultrasound probe 102, outlined by the longitudinal edge of the ultrasound image and the skin contour.

(Analysis for Positional Relationship Determination)

Figure 6A:
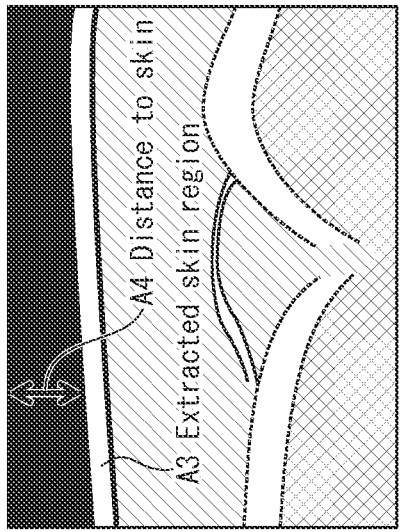
FIGS. 6A-6C illustrate a subject of analysis for positional relationship determination.
Figure 6B:
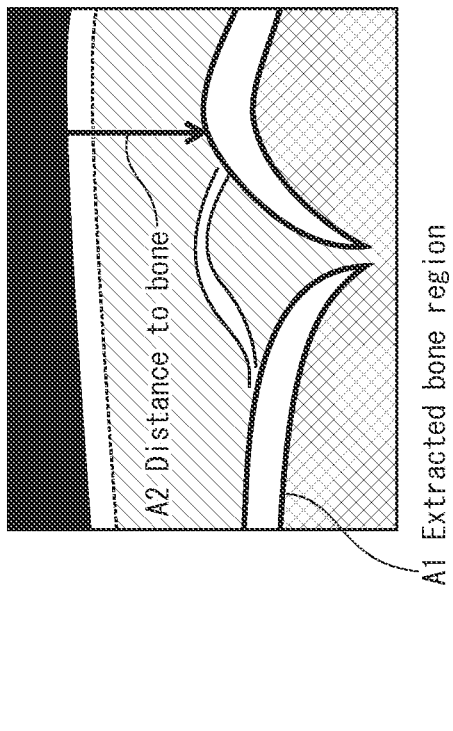
Figure 6C:
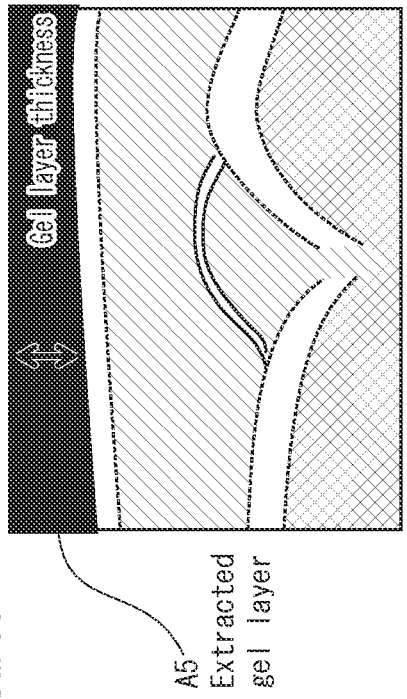
Figure 8A:
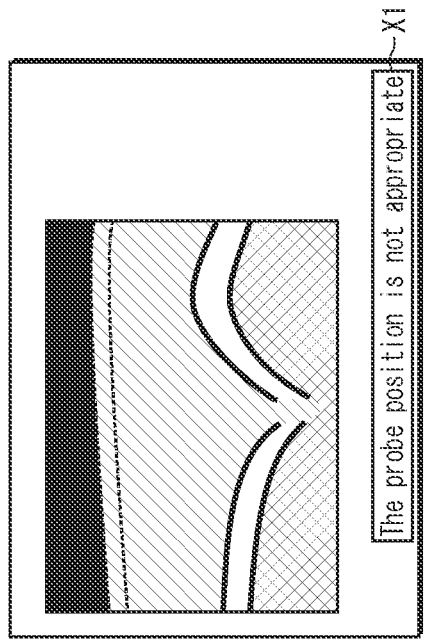
FIGS. 8A and 8B illustrate a first example of positional relationship notification.
Figure 8B:
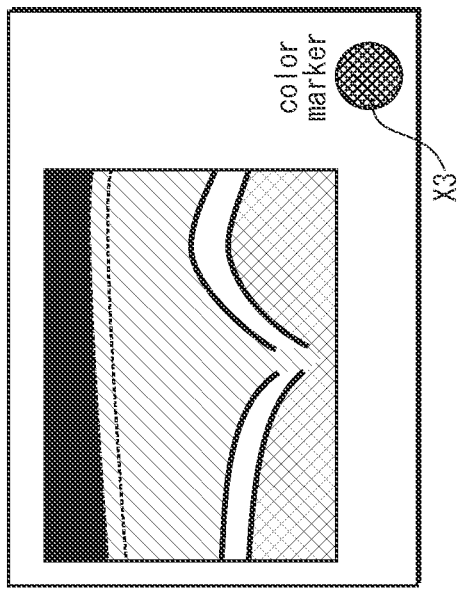
Figure 8C:
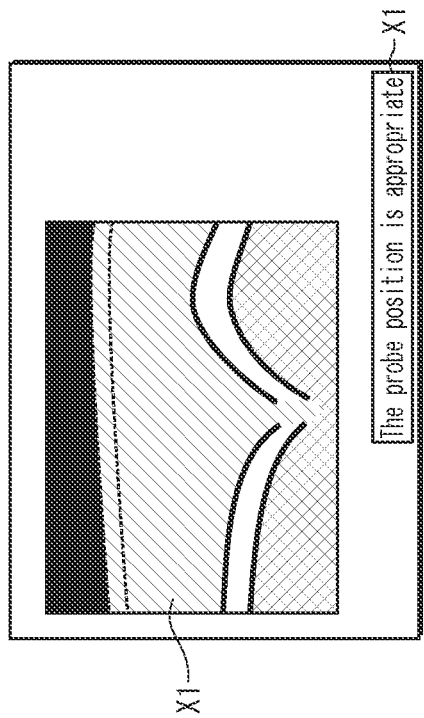
FIG. 8C illustrates a second example of positional relationship notification.

The subject of analysis for positional relationship determination is described below. FIGS. 6A-6C illustrate a subject of analysis for the positional relationship determination. The subject of analysis for positional relationship determination includes a short-axis distance from the longitudinal edge to the bone contour (see FIG. 6A), a distance from the longitudinal edge to the skin contour (see FIG. 6B), and a continuous length of a low-luminance region in the short-axis direction (see FIG. 6C). In FIG. 6A, a bone region A1 has been extracted by the ultrasound diagnostic device and a continuous length A2 extends from the longitudinal edge to the bone region A1. In FIG. 6B, skin region A3 has been extracted by the ultrasound diagnostic device and continuous length A4 extends from the longitudinal edge to the skin region A3. In FIG. 8C, a continuous length A5 extends in the short-axis direction through the low-luminance pixel region measured by the ultrasound diagnostic device. In the present Embodiment, the device is able to determine whether or not the positional relationship of the ultrasound probe 102 is appropriate.

(Gel Layer Shape)

The shape of the gel layer and of the body surface appearing in the image is described next. A measurement position appearing in the image has a contour that takes on various shapes. Some increase monotonically along the longitudinal axis, while others decrease monotonically. Some are horizontal while others are curves of n-dimensional functions. In such cases, where the shape of the measurement position varies, the thickness of the gel layer must be greater than a predetermined threshold, regardless of the shape of the measurement position. Specifically, a change curve of the skin contour, which is the body surface at the measurement position, is extracted and a minimum difference from the longitudinal axis that exceeds a predetermined threshold is found on the change curve.

An outline of the skin contour appearing in the image is labelled Outline of skin in FIG. 7. The X-axis corresponds to the longitudinal axis of the image and the Y-axis corresponds to the measurement position, such that coordinates (X, Y) on the outline of the skin satisfy $Y=F(x)$. When $Y=F(x)$, an X-coordinate having the smallest Y is calculated, and a determination of ultrasound probe pressure is made according to whether or not the thickness at that X-coordinate is greater than the predetermined threshold. In FIG. 7, pixels P11 and P12 are minima on the longitudinal axis, in terms of gel layer thickness. As such, calculating the minimum point satisfying $Y=F(x)$ results in pixels P11 and P12. The determination of appropriateness for the positional relationship of the ultrasound probe 102 is made by comparing the respective gel layer thickness at pixels P11 and P12 to the threshold.

However, depending on the extraction precision of the body surface outline the minimum may not be calculable in some cases. In the present Embodiment, the determination of whether or not the distance between the longitudinal edge and the outline of the skin exceeds the threshold is made at a plurality of positions along the entirety of the longitudinal axis. That is, the present Embodiment makes the determination regarding the gel layer using requirements such that the distance to the skin exceeds a predetermined threshold at a plurality of locations across the entire region facing the element array of the ultrasound probe 102.

Points labelled Probe Start and Probe End in FIG. 7 indicate the start point and end point, respectively, of the range occupied by the ultrasound probe 102 taking the ultrasound image. Pixels P1, P2, and so on are pixels along the longitudinal axis. Measurement paths for continuous length measurement are indicated by downward arrows. A number of low-luminance pixels from each point P1, P2, and so on to the outline of skin indicates a continuous length of low-luminance pixels. The threshold for comparing the continuous length at each pixel is labelled Thd. In the region located somewhat deeper than the surface of the ultrasound probe 102 (i.e., the region surrounded by the upper longitudinal edge of the ultrasound image and the skin outline), when the continuous length at all pixels exceeds the aforementioned threshold, then the ultrasound probe 102 has an appropriate positional relationship above the skin.

(Threshold for Positional Relationship Determination)

Thresholds for the distance between the ultrasound probe 102 and bone, and for the distance between the ultrasound probe 102 and skin, are described below.

In the present Embodiment, the positional relationship of the ultrasound probe 102 to the body surface is found to be non-appropriate when the distance between the ultrasound probe 102 and the bone is below the threshold of, for example, 2 cm at a plurality of points along the entirety of an array of the ultrasound probe 102, given that pressing the body surface produces pressure effectively aggravating clinical signs. Also, the positional relationship of the ultrasound probe 102 to the body surface is found to be non-appropriate when the distance between the ultrasound probe 102 and the skin is below the threshold of, for example, 2 mm at a plurality of points along the entirety of the array of the ultrasound probe 102, as pressing the body surface produces pressure effectively aggravating clinical signs.

When the ultrasound probe 102 and the skin are separated by 2 mm or more, the thickness of the gel layer filling the space between the ultrasound probe 102 and the skin is likely to also be equal to or greater than 2 mm at each of the positions along the array of the ultrasound probe 102. Accordingly, in the present Embodiment, the determination of whether or not the positional relationship of the ultrasound probe 102 to the body surface is appropriate is made by determining whether a gel layer thick enough to fill the space between the ultrasound probe 102 and the skin exceeds the threshold of 2 mm at a plurality of positions along the array of the ultrasound probe 102.

(Positional Relationship Notification Types)

The various types of positional relationship notifications are described next. FIGS. 8A-8D illustrate three variations of positional relationship notification. FIGS. 8A and 8B illustrate a first example of positional relationship notification. When the positional relationship between the ultrasound probe 102 and the body surface has been found appropriate, message X1 is displayed on a screen, reading "The probe position is appropriate" (see FIG. 8A). Conversely, when the positional relationship between the ultrasound probe 102 and the body surface has been found not appropriate, message X1 is displayed on a screen, reading "The probe position is not appropriate" (see FIG. 8B).

Figure 8D:
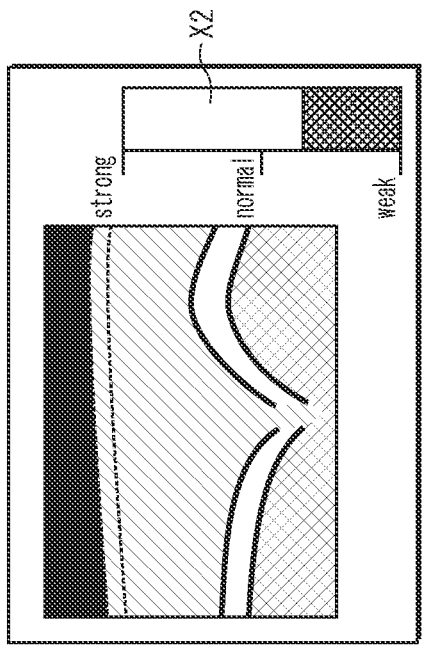
FIG. 8D illustrates a third example of positional relationship notification.

FIG. 8C illustrates a second example of positional relationship notification. In the second example, a bar graph X2 illustrates a degree of appropriateness for the probe position. For instance, the bar graph shows a higher degree when the probe is in a more appropriate position. Also, the colour may change with bar height. For instance, the bar may be red when low (i.e., when the probe position is not appropriate) and become blue and then green as the bar grows taller (i.e., when the probe position is appropriate). FIG. 8D illustrates a third example. In the third example, a colour marker X3 illustrates the degree of appropriateness for the probe position. For instance, the colour marker may be blue or green when the probe position is appropriate, and may be red when the probe position is not appropriate. This concludes the explanation of positional relationship notification types.

(Internal Configuration of Ultrasound Diagnostic Device 101)

The detailed internal configuration of the ultrasound diagnostic device 101 is described next.

Figure 9A:
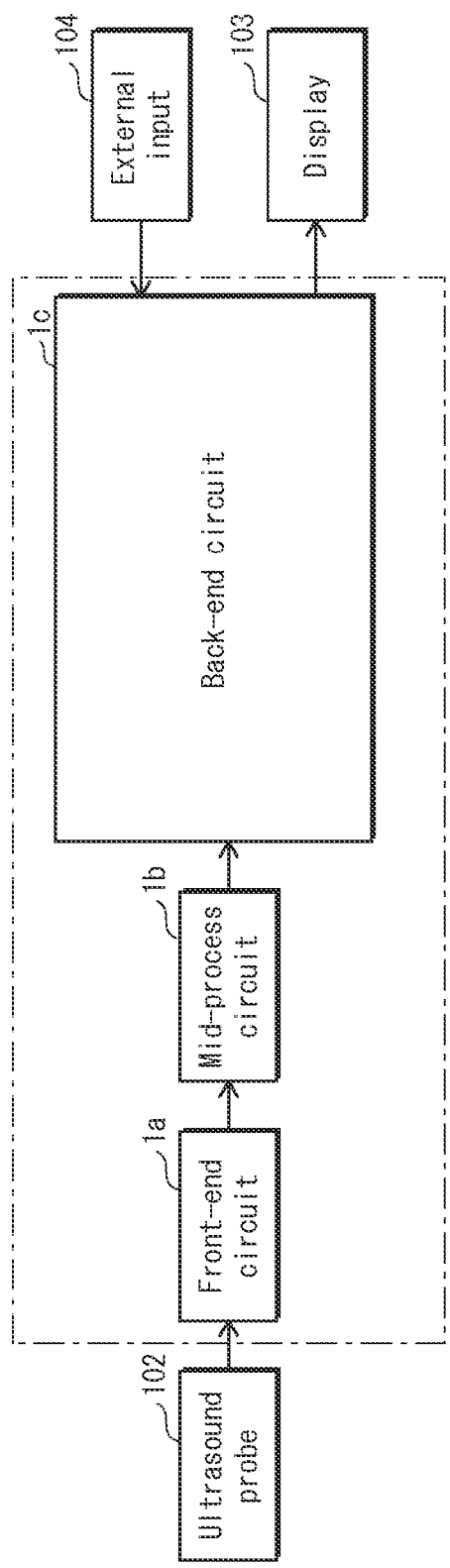
FIG. 9A illustrates the hardware configuration of the ultrasound diagnostic device.

FIG. 9A illustrates the hardware configuration of the ultrasound diagnostic device 101. As shown, the ultrasound diagnostic device 101 includes a front-end circuit 1*a*, a mid-process circuit 1*b*, and a back-end circuit 1*c*.

The front-end circuit 1*a* causes the ultrasound probe 102 to perform transmission and reception of the ultrasound, acting as an interface circuit performing signal input and output with respect to the ultrasound probe 102.

The mid-process circuit 1*b* includes an arithmetic operation circuit, a sum-product operation circuit, and a shifter circuit, acting as a dedicated circuit element for performing ultrasound image generation and other processing relating to the ultrasound image.

The back-end circuit 1*c* is a component of a computer system including a microprocessor unit (hereinafter, MPU), read-only memory (hereinafter, ROM), random access memory (hereinafter, RAM), and an interface circuit.

Figure 9B:
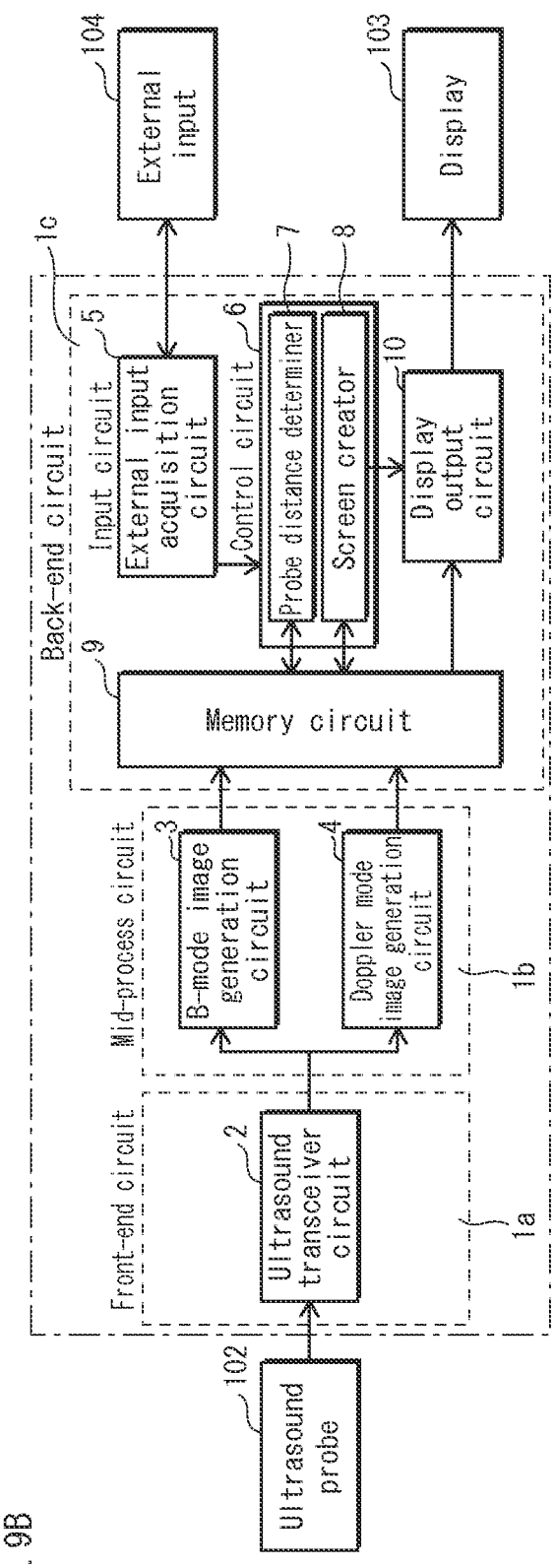
FIG. 9B illustrates the internal configuration of the ultrasound diagnostic device pertaining to Embodiment 1.

FIG. 9B is a block diagram of the internal configuration of the ultrasound diagnostic device 101 in terms of processing content.

FIG. 9B pertains to the internal configuration of the ultrasound diagnostic device 101 of Embodiment 1. The ultrasound diagnostic device 101 of Embodiment 1 includes an ultrasound transceiver circuit 2, a B-mode image generation circuit 3, a Doppler mode image generation circuit 4, an external input acquisition circuit 5, a control circuit 6 (which includes a probe distance determiner 7 and a screen creator 8), a memory circuit 9, and a display output circuit 10.

The ultrasound transceiver circuit 2 inputs an ultrasound received by the ultrasound probe 102 as an ultrasound reception signal, and outputs the ultrasound as an ultrasound echo signal after applying processes of beam forming, detection, logarithmic compression, and so on.

The B-mode image generation circuit 3 applies the processes of beam forming, detection, logarithmic compression, and so on to the ultrasound echo signal input from the ultrasound transceiver circuit 2, to generate the B-mode image. The B-mode image generated by the B-mode image generation circuit 3 is temporarily stored.

The Doppler mode image generation circuit 4 performs an autocorrelation operation on the ultrasound echo signal input by the ultrasound transceiver circuit 2 and, upon converting the result into a flow speed, extracts a speed component indicating a blood flow component by using filtering. The Doppler mode image generation circuit 4 then calculates an average speed, spread, and power of the blood flow component obtained through filtering, and generates the Doppler mode image.

The external input acquisition circuit 5 selects valid user input, with respect to a screen layout displayed on the display 103, among external input made to the external input 104, outputs the selection to the control circuit 6, and causes the control circuit 6 to execute a screen update in accordance with the user input.

The control circuit 6 performs overall control of the ultrasound diagnostic device 101 in accordance with the user input output from the external input acquisition circuit 5. This involves creating a screen layout required for displaying the B-mode image and the Doppler mode image, performing initial display of the screen layout, and updating the screen layout in accordance with the user input received by the external input acquisition circuit 5. The appropriateness of the positional relationship between the ultrasound probe 102 and the body surface is displayed on the screen layout. The control circuit 6 includes the probe distance determiner 7 and the screen creator 8 in order to perform the aforementioned processes.

The probe distance determiner 7 uses the B-mode image and the Doppler mode image stored in the memory circuit 9 to determine whether or not the positional relationship between the body surface and the ultrasound probe 102 is appropriate, by measuring the distance from the surface of the ultrasound probe 102 to the skin or the bone.

The screen creator 8 creates the screen layout for receiving interactive operations pertaining to the ultrasound image when the display unit 103 displays the B-mode image and the Doppler mode image. The screen layout includes content assisting the ultrasound diagnostic, such as an operator name, a patient name, time information, ultrasound diagnostic device setting information, a message, a bar graph, a colour mark, and so on. The screen layout also includes an indicator indicating the appropriateness of the positional relationship between the probe and a measurement target. The message changes in accordance with the indicator, as does the position of the bar in the bar graph.

The memory circuit 9 writes one screen of pixel data for the B-mode image generated by the B-mode image generation circuit 3 and the Doppler mode image generated by the Doppler mode image generation circuit 4, and supplies the data for processing by the probe distance determiner 7 and the screen creator 8. The memory circuit 9 also stores the screen layout created by the screen creator 8.

The display output circuit 10 includes a superposition circuit superposing the screen layout created by the screen creator 8 on a video signal for display by the display unit 103, and notifies the user of determination results regarding the appropriateness of the positional relationship.

This concludes the explanation of the ultrasound diagnostic device 101 components.

(Detailed Configuration of Probe Distance Determiner 7)

Figure 10:
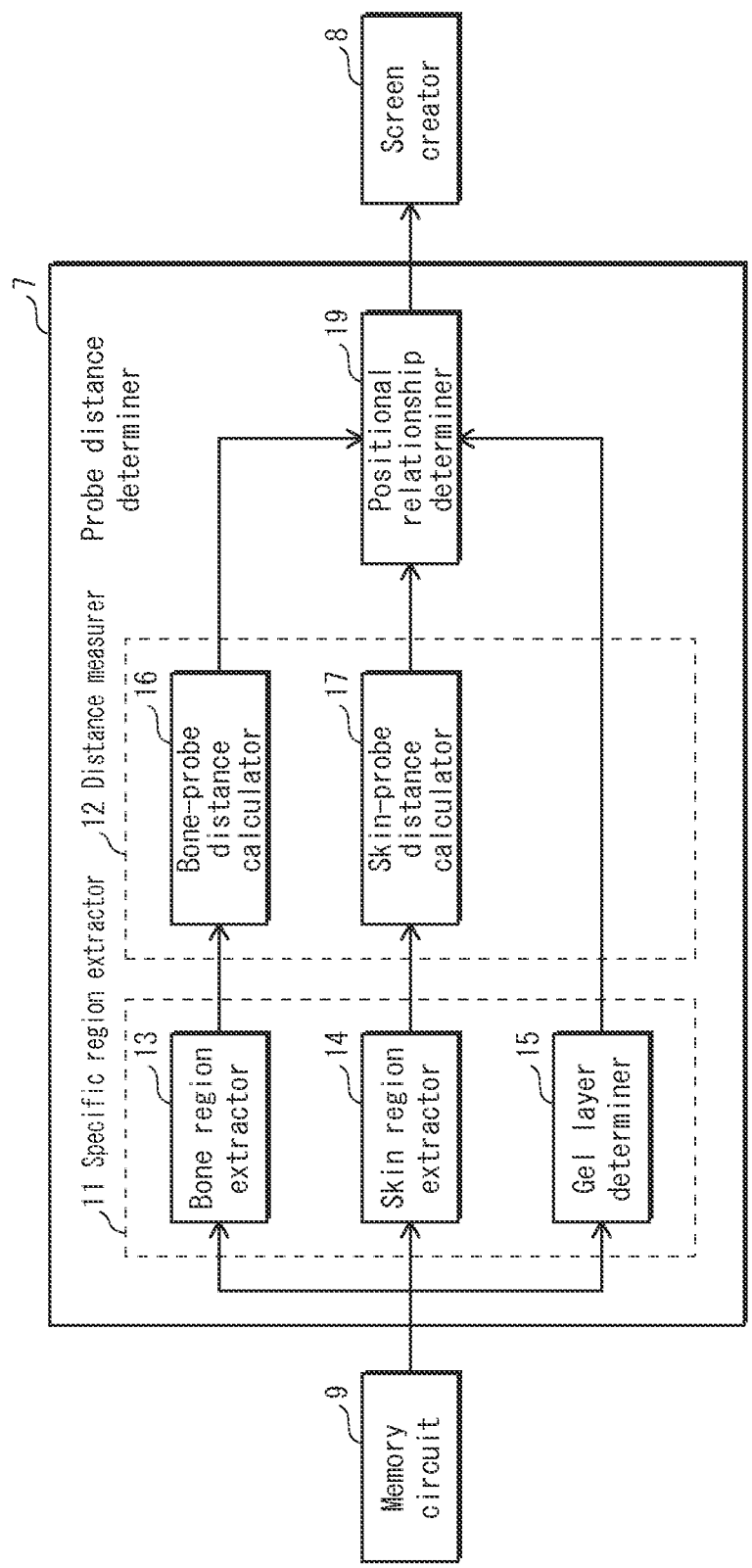
FIG. 10 illustrates the internal configuration of a probe distance determiner 7.

The detailed internal configuration of the probe distance determiner 7 is described next. FIG. 10 shows the internal configuration of the probe distance determiner 7. As shown, the probe distance determiner 7 includes a specific region extractor 11 and a distance measurer 12. The specific region extractor 11 in turn includes a bone region extractor 13, a skin region extractor 14, and a gel layer determiner 15. The distance measurer includes a bone-probe distance calculator 16, and a skin-probe distance calculator 17. The results calculated by the bone-probe distance calculator 16 and the skin-probe distance calculator 17 are used to produce determination results pertaining to the positional relationship between the ultrasound probe 102 and the body surface. Thus, a positional relationship determiner 19 is provided within the probe distance determiner 7.

The bone region extractor 13 extracts a bone region. The extraction method may involve extracting high-luminance portions (1), matching a template (2), detecting a bone through machine learning methods (3), and so on.

The skin region extractor 14 extracts a skin region. The extraction method may involve extracting a horizontal line in an upper part of the screen (1), matching a template (2), using machine learning (3), and so on.

The gel layer determiner 15 determines whether or not a region having a luminance distribution unique to the gel layer is present within the region located somewhat deeper than the surface of the ultrasound probe 102 (i.e., the region surrounded by the upper longitudinal edge of the ultrasound image and the skin outline). The determination method makes use of the fact that the gel layer is a uniform, low-luminance region. In some cases, there may be some luminance due to multi-reflection of the ultrasound from the ultrasound probe 102 along the longitudinal axis of the B-mode image and the Doppler mode image. The gel layer determiner 15 avoids the effect of this multi-reflection by excluding a few lines of pixels at the upper edge of the longitudinal axis from the range of gel layer extraction. Thus, the determination of whether or not the gel medium is present is made accurate.

The bone-probe distance calculator 16 calculates the distance from the upper outline of the extracted bone region to the upper longitudinal edge of the ultrasound image (i.e., the probe surface).

The skin-probe distance calculator 17 calculates the distance from the upper outline of the extracted skin region to the upper longitudinal edge of the ultrasound image (i.e., the probe surface).

The positional relationship determiner 19 provides determination results regarding the appropriateness of the positional relationship between the ultrasound probe 102 and the body surface, according to whether or not the distance from the upper outline of the extracted bone region to the upper longitudinal edge of the ultrasound image is equal to or greater than the threshold and whether or not the distance from the upper outline of the extracted skin region to the upper longitudinal edge of the ultrasound image is equal to or greater than the threshold.

This concludes the explanation of the probe distance determiner 7 components. The machine learning method and pattern matching suggested in the description of probe distance determiner 7 components are described next.

In a machine learning method, a sample sorted into bone portions and skin portions and a sample sorted into non-bone portions and non-skin portions are prepared in advance to generate an identifier. Once a new image is obtained, the identifier is applied to each of a plurality of local regions making up the image, and performs detection of bone regions or of skin regions.

In a pattern matching method, a representative skin region or bone region is stored in advance as a template. The template is, for example, an average image. Then, once a new image is obtained, matching of rigid or non-rigid bodies using the registered template and a plurality of local regions making up the new image. Bone regions and skin regions are then extracted from the local regions, according to the matching results.

This concludes the explanation of the ultrasound diagnostic device 101 components.

(Processing)

The components of the ultrasound diagnostic device 101 described thus far perform functions according to various conditions and internal device parameters. The processing performed by the hardware resources is generalizable as follows. The generalised processing is described with reference to flowcharts of FIGS. 11-15. The processing performed by the components of the ultrasound diagnostic device 101 is described with reference to the flowcharts.

Figure 11:
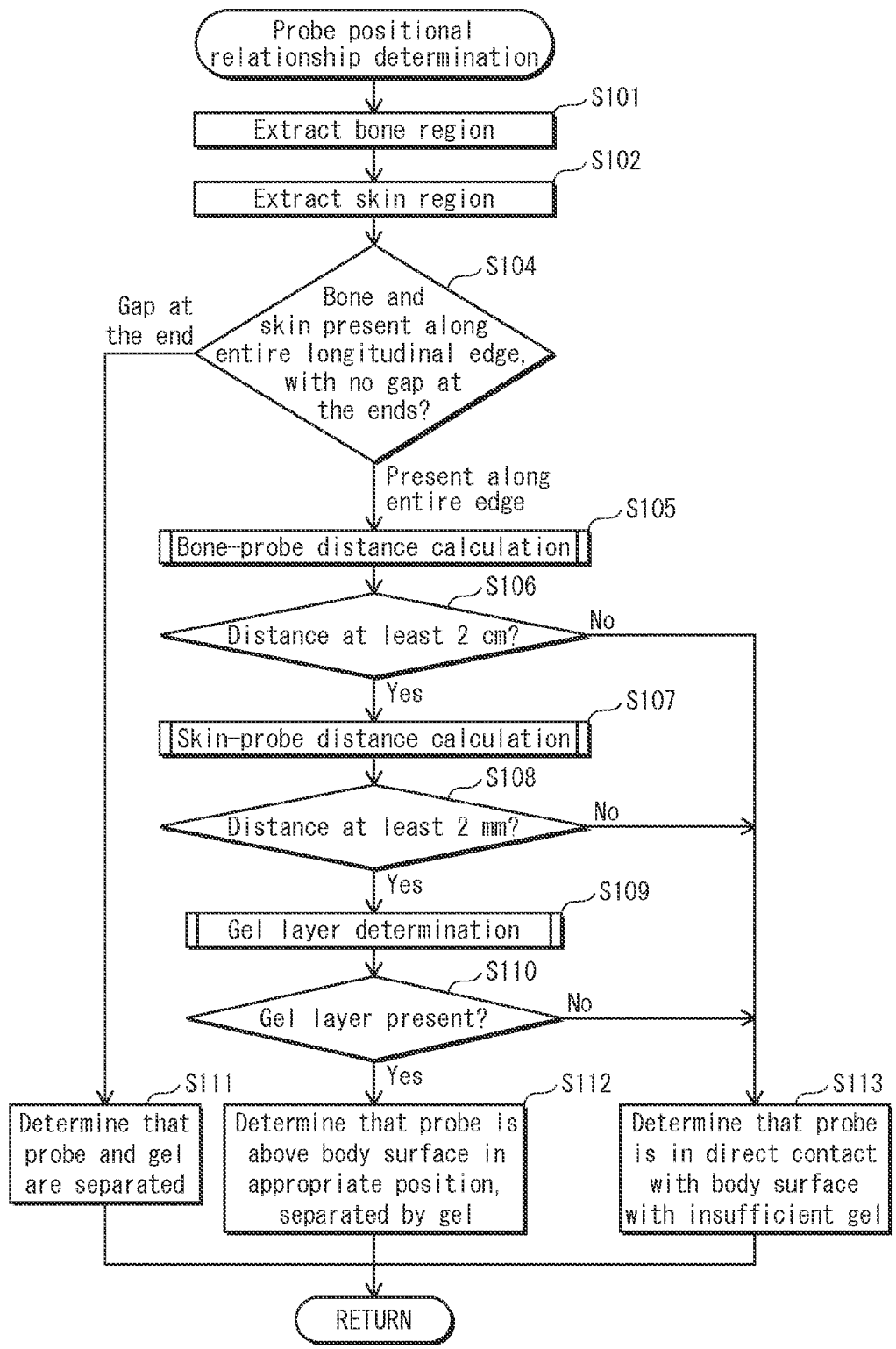
FIG. 11 is a flowchart of an example of a positional relationship determination process for the probe.

FIG. 11 is a flowchart showing an example of the positional relationship determination process for the ultrasound probe

102. The process begins with step S101, in which a bone region is extracted from the image, followed by step S102, in which a skin region is extracted. The process then advances to steps S104 through S113.

In step S104, a determination is made regarding whether or not the bone region and the skin region are absent at any end along the entirety of the longitudinal axis. In step S105, the distance between the bone and the ultrasound probe is calculated. In step S106, a determination is made regarding whether or not the distance calculated in step S105 satisfies the standard of 2 cm.

In step S107, the distance between the skin and the ultrasound probe is calculated. In step S108, a determination is made regarding whether or not the distance calculated in step S107 satisfies the standard of 2 mm.

In step S109, a gel layer determination process is performed. In step S110, a determination regarding whether or not the gel layer is present in the region located somewhat deeper than the surface of the ultrasound probe 102 (i.e., the region surrounded by the longitudinal edge of the ultrasound image and the extracted skin region) is made in accordance with the gel layer determination process.

When the result of step S104 is such that absences exist, then in step S111, a determination result is issued such that the positional relationship of the ultrasound probe 102 is distant from the gel.

When any of steps S106, S108, and S110 are affirmative, then in step S112, a determination result is issued such that the positional relationship between the ultrasound probe 102 and the body surface is appropriate as the ultrasound image does not affect the appearance of symptoms. That is, the ultrasound probe 102 is above the body surface with the gel filling the space between the ultrasound probe 102 and the body surface.

When any of steps S106, S108, and S110 are negative (i.e., when the distance between the skin and the ultrasound probe 102 is less than 2 mm, and when the distance between the bone and the ultrasound probe 102 is less than the standard of 2 mm), then a determination result is returned such that the positional relationship between the ultrasound probe 102 and the body surface is not appropriate as the positional relationship affects the appearance of symptoms in the ultrasound image.

With respect to the above-described flowchart, the bone-probe distance calculation in step S105, the skin-probe distance calculation in step S107, and the gel layer determination in step S109 are each realised as subroutines of more detailed processes. These detailed processes are describe with reference to the flowcharts of FIGS. 12-14.

Figure 12:
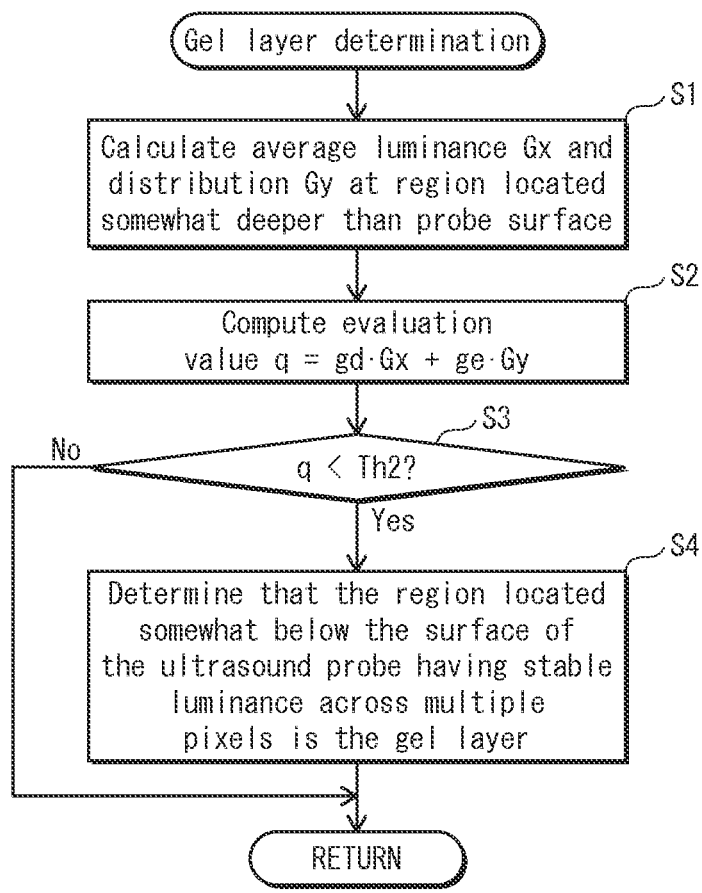
FIG. 12 is a flowchart of an example of gel layer determination processing.

FIG. 12 is a flowchart of an example of gel layer determination processing. First, with respect to the region that is somewhat deeper than the surface of the ultrasound probe 102 ((i.e., the region surrounded by the upper longitudinal edge of the ultrasound image and the skin outline), an average luminance value Gx and a dispersion Gy are calculated (step S1), an average value q is calculated by computing $q = gd \cdot Gx + ge \cdot Gy$ (step S2), and an evaluation is performed to determine whether or not the value q satisfies $q < Th2$ (step S3). When the determination is affirmative, a determination is made that the gel layer is present in the region somewhat below the surface of the ultrasound probe with luminance that is stable across multiple pixels (step S4), followed by a return. Step S4 is skipped when the result of Step S3 is NO.

Figure 13:
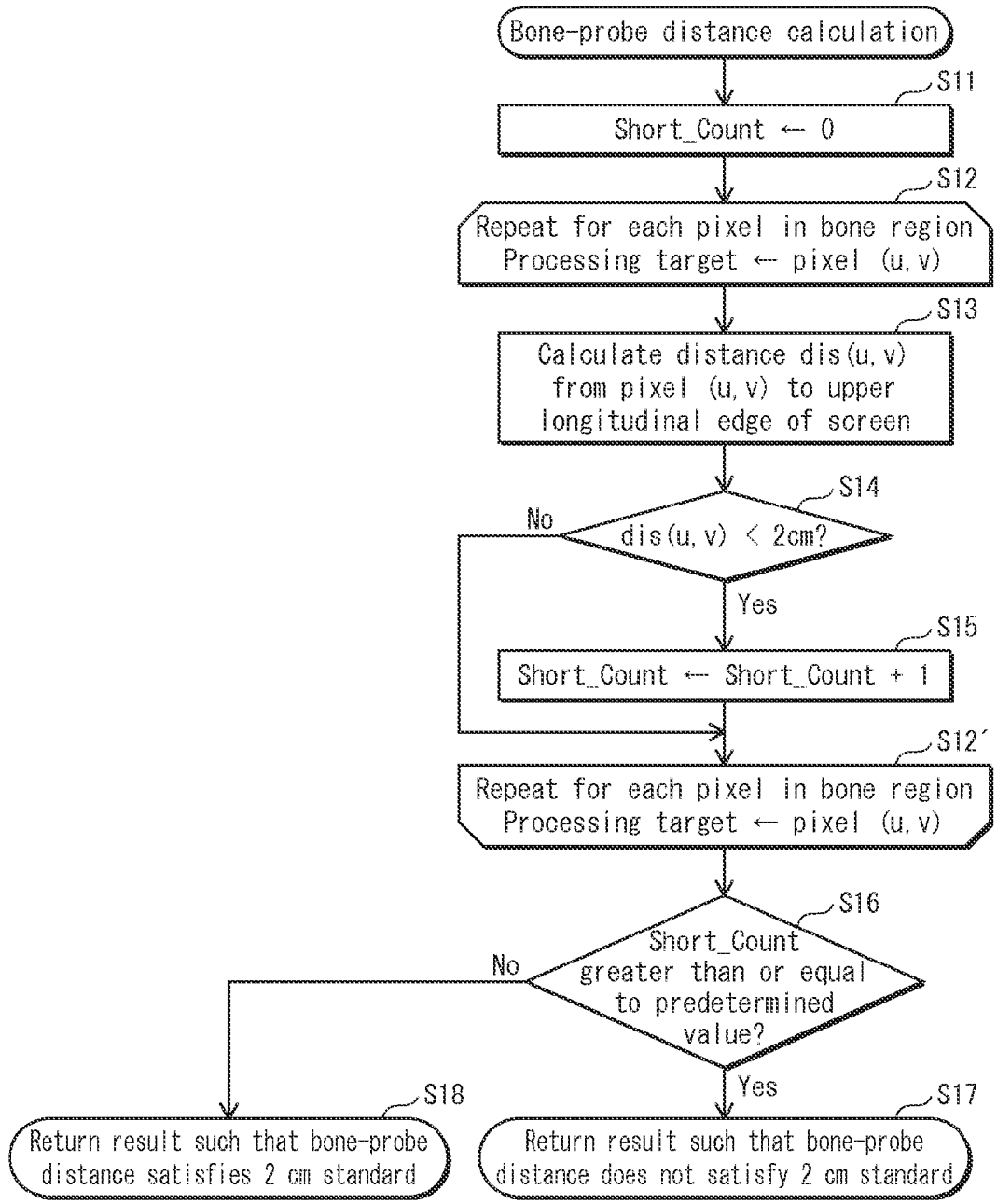
FIG. 13 is a flowchart of an example of bone-probe distance calculation processing.

FIG. 13 is a flowchart of an example of bone-probe distance calculation processing. Here, the variable Short_Count is a count of pixels at a short distance from the ultrasound image. The flowchart begins with step S11, in which Short-_Count is initialised at one. The process then performs a loop from step S12 to step S12'. The loop involves calculating, for each pixel in the bone region, a distance $dis(u,v)$ from a pixel $(u,v)$ to the longitudinal edge (step S13), a determination of whether or not $dis(u,v)$ satisfies a threshold of 2 cm (step S14), and incrementing Short_Count in the negative case (step S15). These steps are repeated for all pixels of the longitudinal edge. Upon leaving the loop, a determination is made in step S16 regarding whether or not Short_Count covers at least a predetermined number of pixels.

When the result of step S16 is YES, then in step S17, a determination result is returned such that the distance between the bone and the ultrasound probe 102 does not satisfy the standard of 2 cm. When the result of step S16 is NO, then in step S18, a determination result is returned such that the distance between the bone and the ultrasound probe 102 satisfies the standard of 2 cm.

The quantity of pixels used for Short_Count comparison may be one or two pixels, or may be 10 or 20 pixels. Comparing the pixel quantities enables that the positional relationship determination is not affected by having too few pixels in cases where the calculated distance where the pixels are found on the bone contour is too short.

Figure 14:
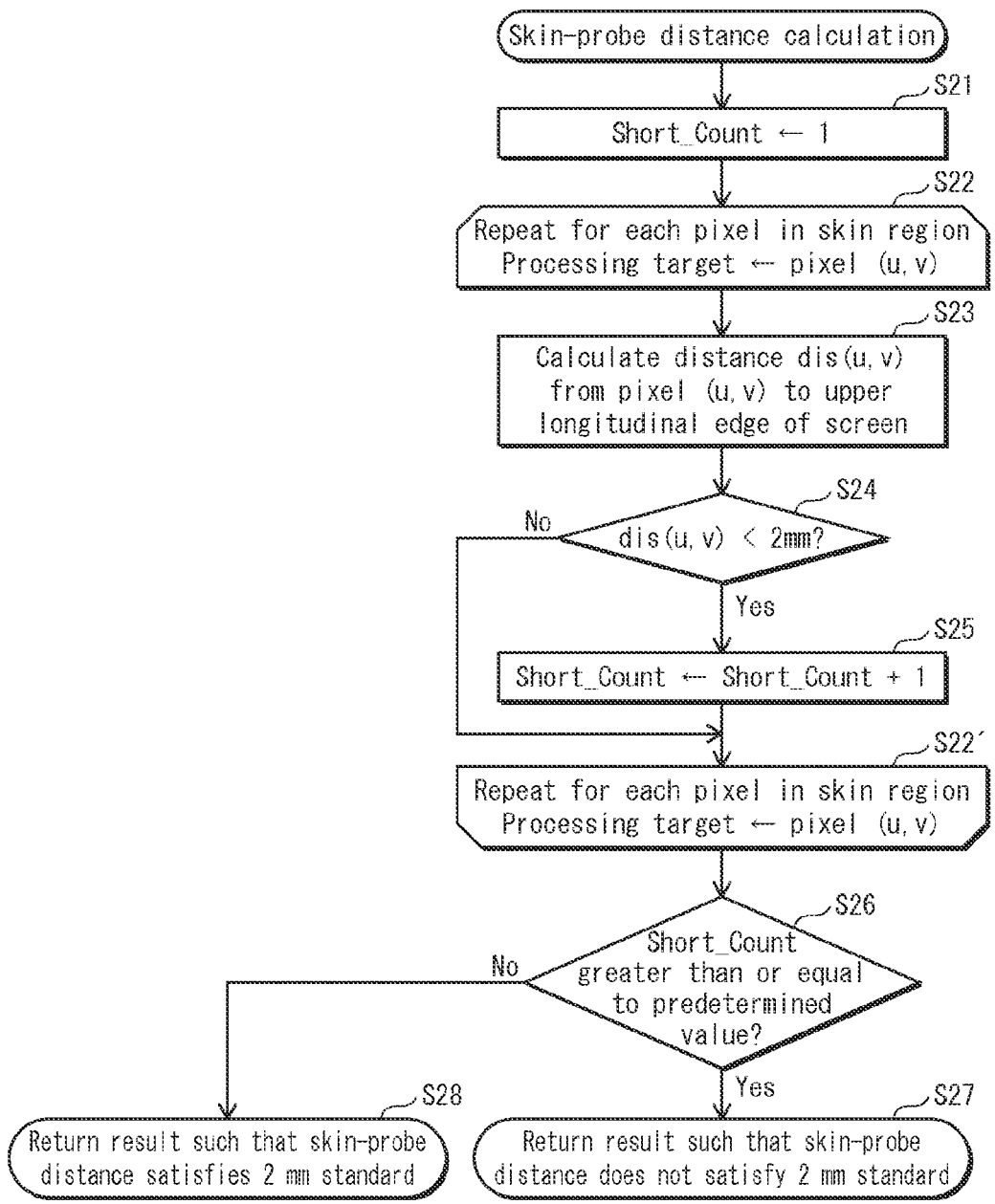
FIG. 14 is a flowchart of an example of skin-probe distance calculation processing.

FIG. 14 is a flowchart of an example of skin-probe distance calculation processing. This flowchart is based on the flowchart of FIG. 13. The points of difference between the respective flowcharts of FIGS. 13 and 14 are in the loop, namely steps S12-S15 in FIG. 13, replaced by steps S22-S25 in FIG. 14. Specifically, step S15 is replaced by step S25.

Steps S12-S15 of FIG. 13 and steps S22-S25 of FIG. 14 differ in that, in FIG. 13, the loop is applied to each pixel on the bone contour, while in FIG. 14, the loop is applied to each pixel on the skin contour.

The difference between step S15 of FIG. 13 and step S25 of FIG. 13 is that in step S15, the determination concerns whether or not the pixels satisfy a distance of 2 cm from the longitudinal edge, while in step S25, the determination concerns whether or not the pixels satisfy a distance of 2 mm from the skin contour.

According to the above-described Embodiment, a determination is made regarding whether or not the gel layer is serving as a cushion, according to the positional relationship of the ultrasound probe as applied to the body surface through the gel. The results are presented as superposed on a screen. When seeking the degree of inflammation in a joint, the operator is informed of whether or not the degree of contact by the probe (i.e., of pressure) is appropriate, and is thus able to adjust the probe application so that appropriate pressure is applied. As such, the probe is applied in the same manner despite different operators performing the application.

(Embodiment 1 Variations)

In Embodiment 1, a determination is made regarding whether or not the low-luminance pixel region is present opposite the acoustic element array of the ultrasound probe 102. However, no such limitation is intended. When a predetermined amount of line pixel data at the longitudinal edge of the frame image includes low-luminance pixels, and those pixels are of uniform luminance, then the determination may also be made regarding the presence of the gel layer.

During frame image generation, the line pixel data are generated through a conversion process from a piece of ultrasound echo data to amplitude data. The low-luminance pixel region is present at the longitudinal edge of the frame image. As such, a determination is made regarding whether or not each piece of line pixel data along the longitudinal edge is made up of a low-luminance pixel region and whether these pixels are of uniform luminance.

When the line pixel data at any location along the longitudinal edge of the ultrasound image does not satisfy the requirement, the line pixel data is not stored for one frame. A determination result is returned such that the positional relationship between the ultrasound probe 102 and the area subject to measurement is not appropriate, and the frame image to which the line pixel data belongs is discarded.

When the line pixel data satisfies the requirement at all locations along the longitudinal edge of the ultrasound image, then a determination result is returned at the line pixel data generation stage, such that the positional relationship between the ultrasound probe 102 and the area subject to measurement is appropriate.

In such an application, a determination is made regarding whether or not the line pixel data composed of low-luminance pixels having uniform luminance extend along the entire longitudinal edge. Thus, there is no need to wait for frame image completion as the determination regarding the positional relationship between the ultrasound probe 102 and the area subject to measurement is made at an earlier stage.

(Embodiment 2)

Embodiment 2 pertains to improvements in terms of calculating a swelling score and an inflammation score for determining whether or not to perform an inflammation quantification on an ultrasound image, followed by performing said inflammation quantification on the ultrasound image. Specifically, Embodiment 1 described real-time processing of an ultrasound image obtained by having a probe transmit and receive ultrasound, to give feedback to a user regarding whether or not the positional relationship between the probe and the body surface is appropriate. In contrast, Embodiment 2 stores a frame image sequence obtained by having the probe transmit and receive the ultrasound, performs ex-post analysis of the frame images, and excludes frame images in which the positional relationship is not appropriate from the inflammation quantification. The frame images in which the positional relationship between the probe and the body surface is appropriate are used for the inflammation quantification, enabling accurate calculation of the swelling score and the inflammation score. Accordingly, images in which new blood vessels within the articular cavity are deformed by pressure applied by the probe are excluded from the calculations of the swelling score and the inflammation score.

(Screen Layout)

The screen layout used in Embodiment 2 is described next. Comparing the screen layout used in Embodiment 2 to the screen layout used in Embodiment 1 reveals that, whereas Embodiment 1 has the display 103 display the appropriateness of the positional relationship between the ultrasound probe 102 and the body surface, Embodiment 2 adds to the display of Embodiment 1 by also displaying the swelling score, the inflammation score, a frame number, and a progress bar for the frame image within the frame sequence.

Figure 15:
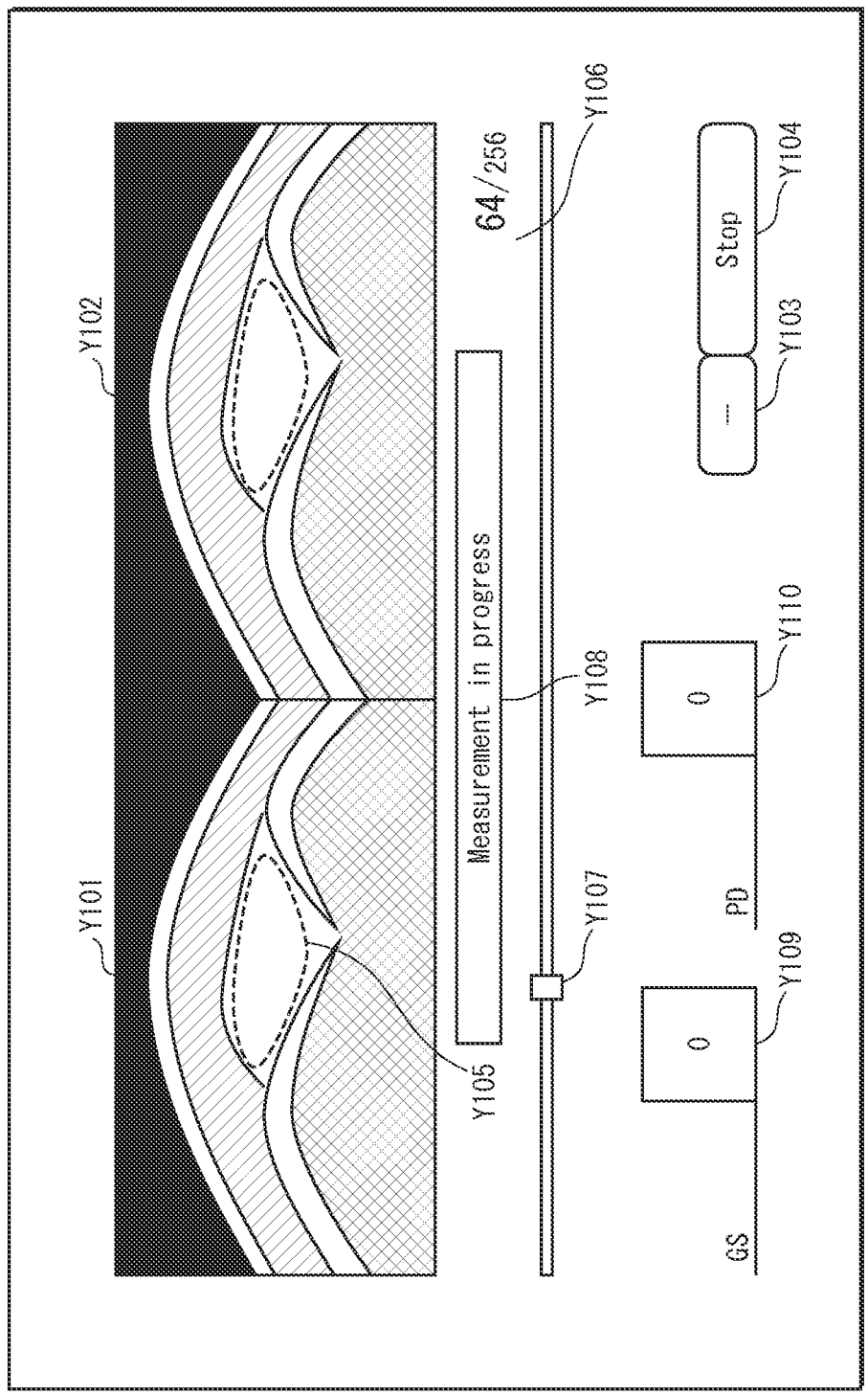
FIG. 15 illustrates an example of a screen layout used in Embodiment 2.
Figure 16:
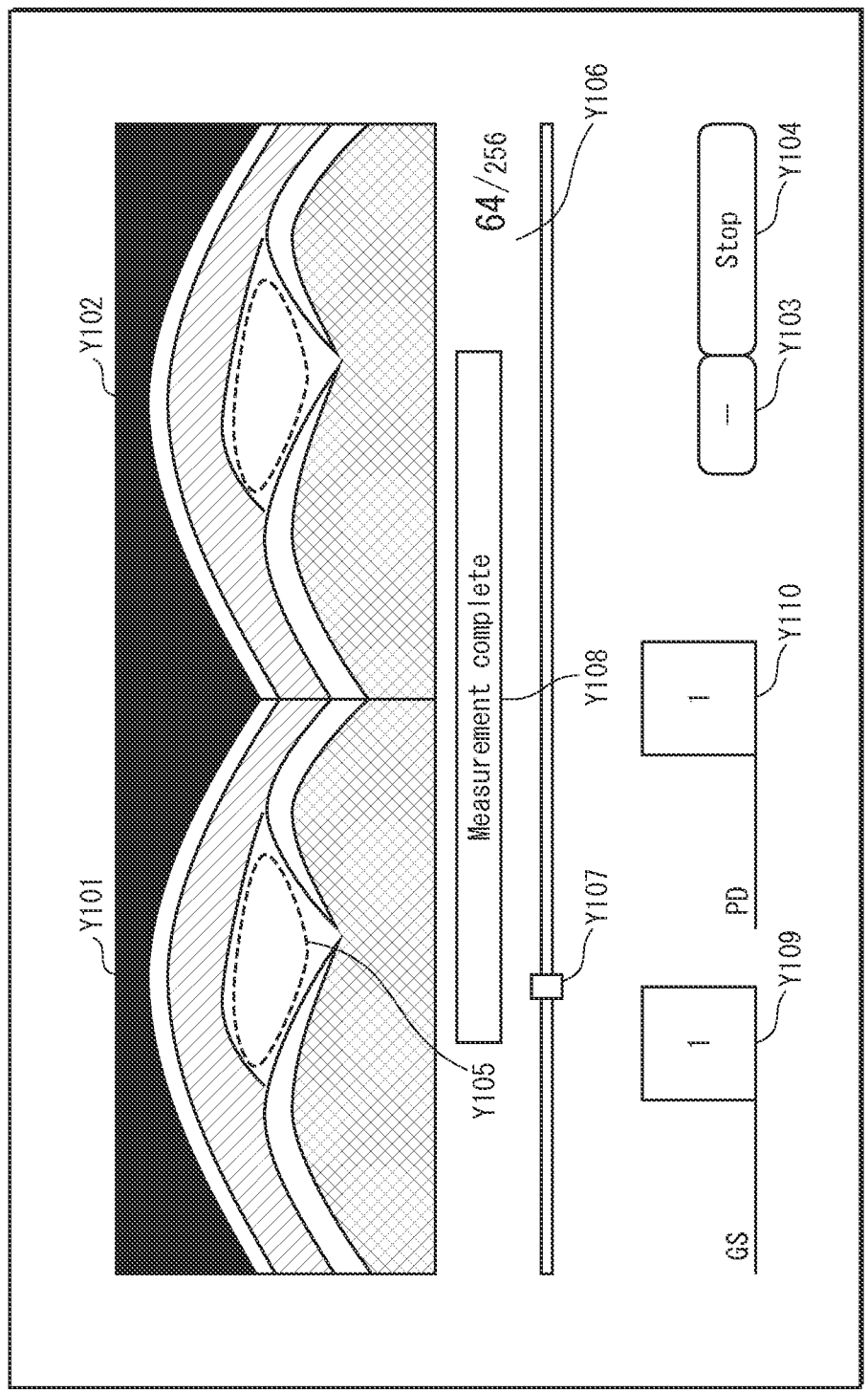
FIG. 16 illustrates an example of the screen layout used in Embodiment 2, after being updated.

FIG. 15 illustrates an example of the screen layout used in Embodiment 2. FIG. 16 illustrates a screen layout having the B-mode image Y 101 and the Doppler mode image Y 102 arranged in an upper half thereof. An articular capsule boundary Y 105 indicates where the blood flow signal is measured. The lower half of the screen layout includes an indicator Y 108 indicating the appropriateness of the positional relationship of the probe, a slider bar Y 107 indicating where the B-mode image Y 101 and the Doppler mode image Y 102 fall in the frame image sequence, and a frame number indicator Y 106 indicating a frame number of the current frame relative to the entire group of frames. Also, the screen layout includes button Y 103 for progressing to the next joint subject to swelling score measurement, and button Y 104 for receiving a command to start or stop measurement.

FIG. 15 depicts a frame image having frame number 64 as the target of inflammation quantification, with the indicator Y 108 having been updated to read "measurement in progress". FIG. 16 illustrates an example of the screen layout used in Embodiment 2 after being updated. FIGS. 15 and 16 differ in the content of the indicator Y 108 and of the swelling score and the inflammation score. The specific differences in the indicator Y 108 are that the indicator Y 108 reads "Measurement in progress" in FIG. 15 and has been updated to read "Measurement complete" in FIG. 16. The specific differences regarding the swelling score and the inflammation score are that in FIG. 15, the swelling score and the inflammation score are both zero, and have been set to one in FIG. 16.

Figure 17:
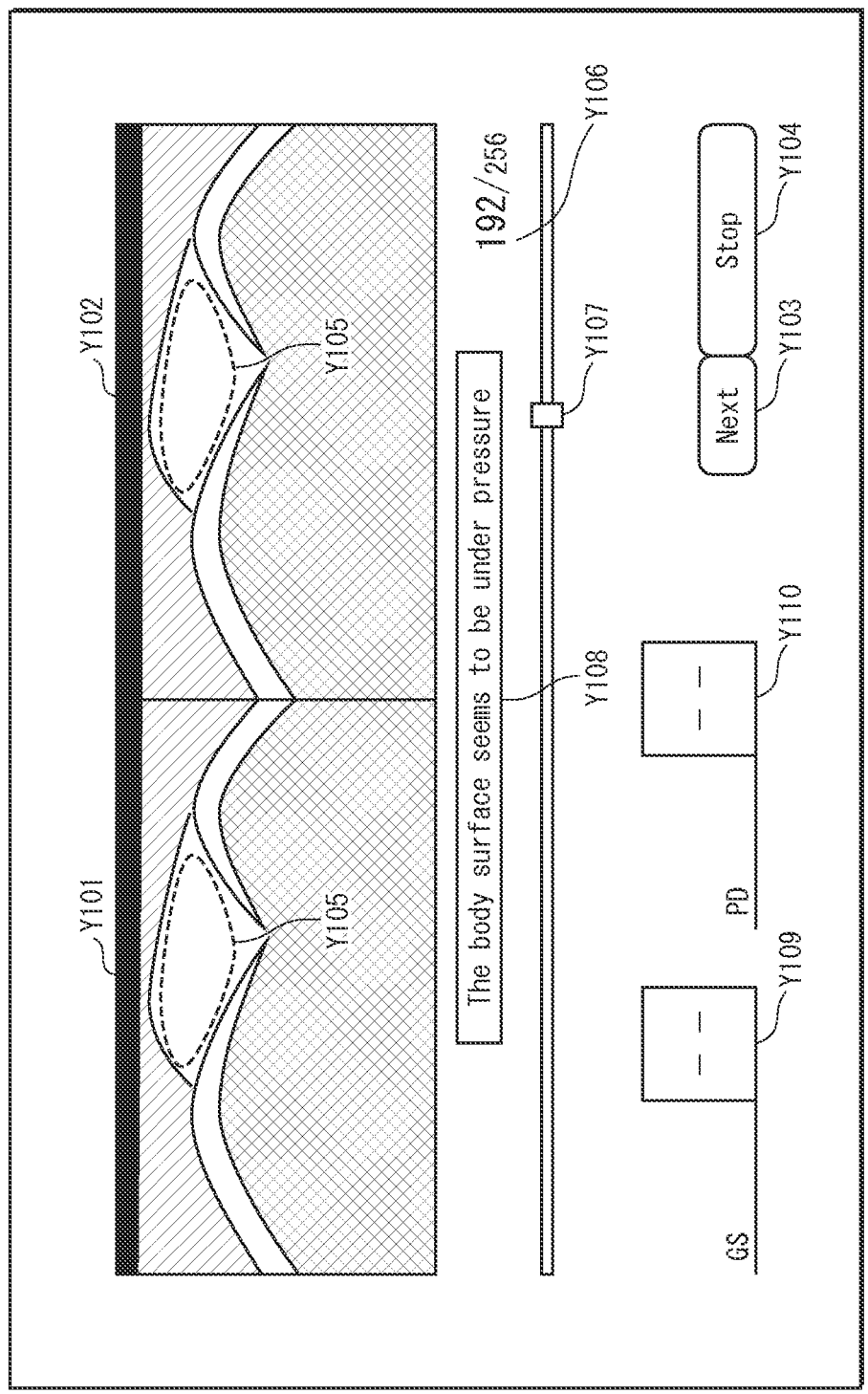
FIG. 17 illustrates an example of a screen layout where the positional relationship between the ultrasound probe 102 and the body surface is not appropriate.

FIG. 17 illustrates an example of a screen layout where the positional relationship between the ultrasound probe 102 and the body surface is not appropriate. As shown, the indicator Y 108 has been updated to read "the body surface seems to be under pressure", thus indicating the effect of the positional relationship between the ultrasound probe 102 and the body surface. Accordingly, a GS score indicator Y 109 and a PD score indicator Y 110 are both blank (i.e., reading - -) to indicate that the frame image current displayed in the screen layout (i.e., frame number 192) is excluded from the inflammation quantification.

The ultrasound diagnostic device 101 pertaining to Embodiment 2 thus performs the above-described screen layout initialisation, then updates the screen layout in accordance with diagnostic process. This concludes the description of the screen layout used in Embodiment 2.

(Internal Configuration of Ultrasound Diagnostic Device 101)

Figure 18:
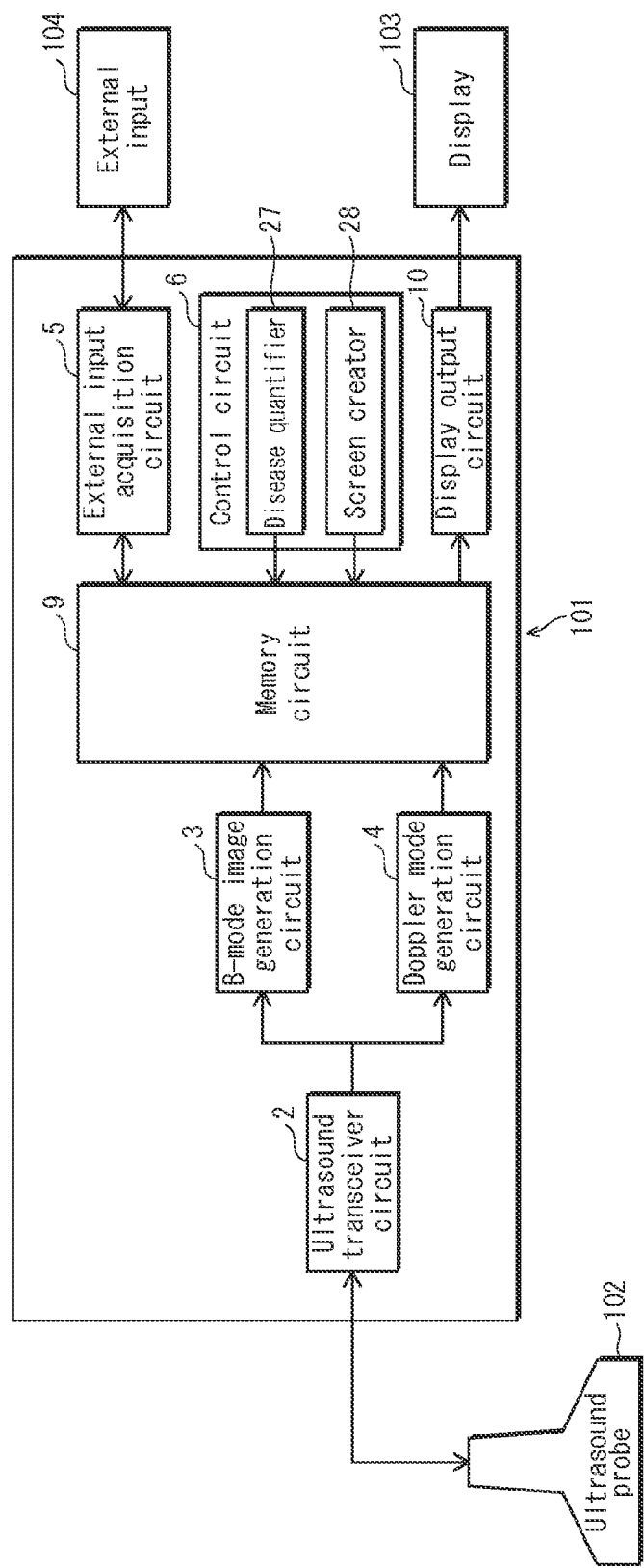
FIG. 18 illustrates the internal configuration of the ultrasound diagnostic device pertaining to Embodiment 2.

The detailed internal configuration of the ultrasound diagnostic device 101 pertaining to Embodiment 2 is described next. FIG. 18 pertains to the internal configuration of the ultrasound diagnostic device of Embodiment 2.

The configuration illustrated in FIG. 18 is based on FIG. 9B. FIG. 18 has the ultrasound transceiver circuit 2, the B-mode image generation circuit 3, the Doppler mode image generation circuit 4, the external input acquisition circuit 5, the memory circuit 9, and the display output circuit 10 in common with FIG. 9B. The points of difference are in the remaining components. Specifically, the probe distance determiner 7 is replaced by a disease quantifier 27, and the screen creator 8 is replaced by a screen creator 28. These new components are described below.

The disease quantifier 27 analyses the B-mode image and the Doppler mode image stored by the memory circuit 9 to quantify a degree of disease progression. The qualification results (i.e., the swelling score and the inflammation score) are stored by the memory circuit 9.

The screen creator 28 creates the screen by overlaying an operator name, a patient name, time information, ultrasound diagnostic device setting information, scores calculated by the disease quantifier 27, and so on, onto the B-mode image or the Doppler mode image stored by the memory circuit 9, for display by the display 103. This concludes the description of the overall configuration of the ultrasound diagnostic device pertaining to Embodiment 2. The disease quantifier 27 serves a major function in the ultrasound diagnostic device pertaining to Embodiment 2. The internal configuration of the disease quantifier 27 is described next.

(Detailed Configuration of Disease Quantifier 27)

Figure 19:
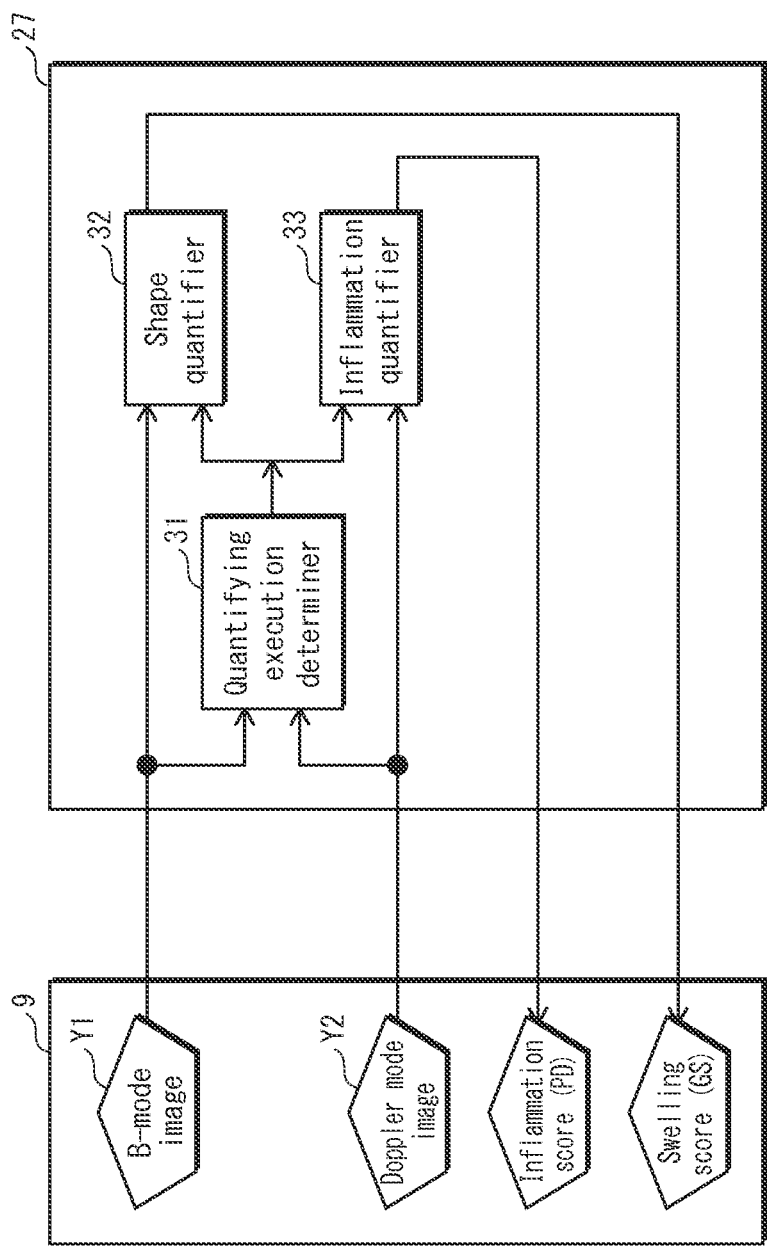
FIG. 19 is a block diagram illustrating details of a disease quantifier 27.

FIG. 19 is a block diagram illustrating the details of the disease quantifier 27. As shown, the disease quantifier 27 includes a quantifying execution determiner 31, a shape quantifier 32, and an inflammation quantifier 33. Here, the B-mode image Y1, the Doppler mode image Y2, the swelling score GS, and the inflammation score PD are associated information, the latter two indicating the degree of disease progression. All of the information is stored by the memory circuit 9.

The quantifying execution determiner 31 takes the B-mode image Y1 and the Doppler mode image Y2 stored by the memory circuit 9 as input, and performs image analysis to determine whether or not the B-mode image Y1 and the Doppler mode image Y2 have been obtained in an appropriate operation. In the affirmative case, the quantifying execution determiner 31 outputs a quantifying execution command to the shape quantifier 32 and the inflammation quantifying 33. In the negative case, a quantifying stop command is output instead.

Once the quantifying execution determiner 31 outputs the quantifying execution command, the shape quantifier 32 calculates the swelling score from a pattern of luminance in the articular cavity and the bone as shown in the B-mode image. The calculated swelling score (also, GS score) is stored by the memory circuit 9. When the quantifying execution determiner 31 outputs the quantifying stop command, the quantifying is not executed and the swelling score is invalidated.

Once the quantifying execution determiner 31 outputs the quantifying execution command, the inflammation quantifier 33 calculates the inflammation score according to the size of a blood flow signal in the articular capsule from the Doppler mode image Y2. The calculated inflammation score (also, PD score) is stored by the memory circuit 9. When the quantifying execution determiner 31 outputs the quantifying stop command, the quantifying is not executed and the inflammation score is invalidated.

This concludes the description of the disease quantifier 27 configuration.

(Detailed Configuration of Quantifying Execution Determiner 31)

Figure 20:
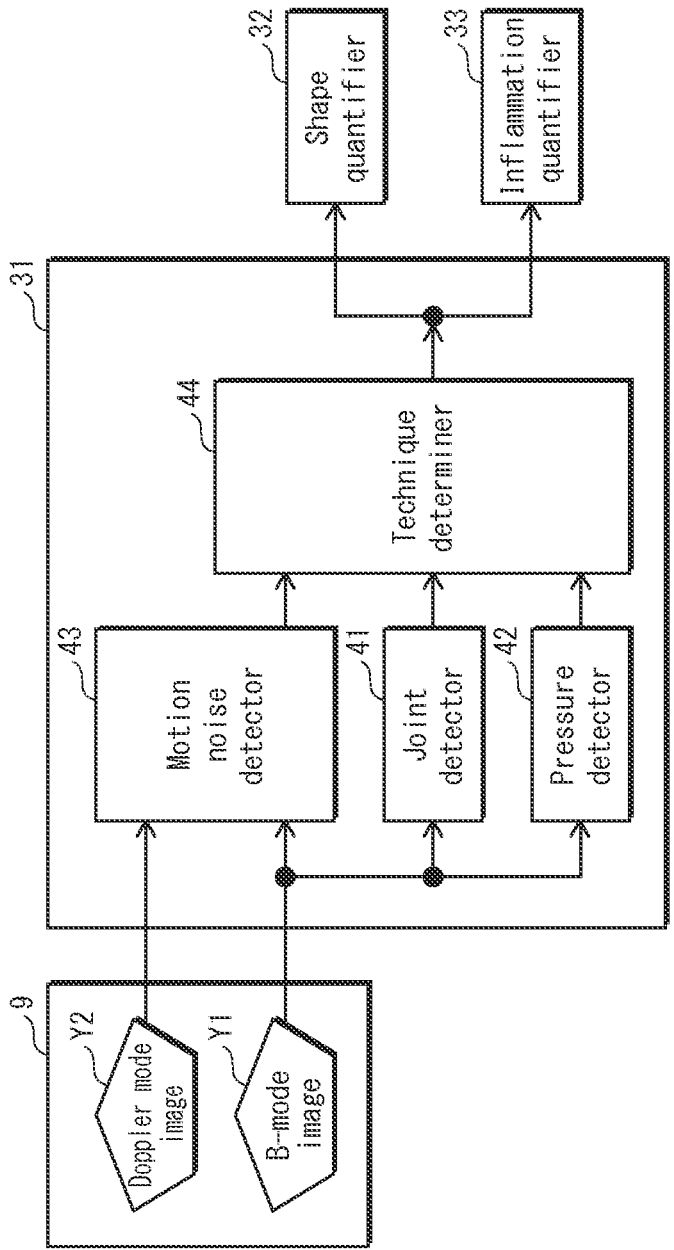
FIG. 20 is a block diagram illustrating details of a quantifying execution determiner 31.

The detailed internal configuration of the quantifying execution determiner 31 is described next. FIG. 20 is a block diagram illustrating the details of the quantifying execution determiner 31. The quantifying execution determiner 31 includes a joint detector 41, a pressure detector 42, a motion noise detector 43, and a technique determiner 44. The B-mode image Y1 and the Doppler mode image Y2 are related information used by these components. All of the information is stored by the memory circuit 9.

The joint detector 41 takes the Doppler mode image stored by the memory circuit 9 as input, and performs bone quality detection and articular capsule detection on the Doppler mode image. The determination result is one of "articular capsule present" and "articular capsule absent", which is then output to the technique determiner 44.

The pressure detector 42 takes the Doppler mode image stored by the memory circuit 9 as input and determines whether or not the probe is applying pressure to the body surface. The determination result is one of "pressure present" and "pressure absent", which is then output to the technique determiner 44.

The motion noise detector 43 takes the Doppler mode image stored by the memory circuit 9 as input, and determines whether or not a Doppler signal based on the Doppler mode image is causing motion noise. The determination result is one of "motion noise present" and "motion noise absent", which is then output to the technique determiner 44. Motion noise is produced by rapid motion of the probe. When the ultrasound is transmitted and received while the probe is in motion, no ultrasound image can be generated from the reflection due to the probe motion being too rapid. The motion noise detector 43 makes a notification as described above, in order to exclude B-mode images and Doppler mode images affected by motion noise.

The technique determiner 44 takes the respective results from the joint detector 41, the pressure detector 42, and the motion noise detector 43 as input. When the results are "articular capsule present", "pressure absent" and "motion noise absent", the image is deemed to have been acquired using appropriate technique. A quantifying execution command is then output to the shape quantifier 32 and to the inflammation quantifier 33. For any other results, the quantifying stop command is output. This concludes the description of the quantifying execution determiner 31 configuration.

(Detection Operations by Joint Detector 41)

The quantifying execution determiner 31 is greatly dependent on the precision of bone cortex detection and of articular cavity detection by the joint detector 41. The bone cortex detection process and the articular cavity detection process by the joint detector 41 are described next, with reference to the drawings.

Figure 21A:
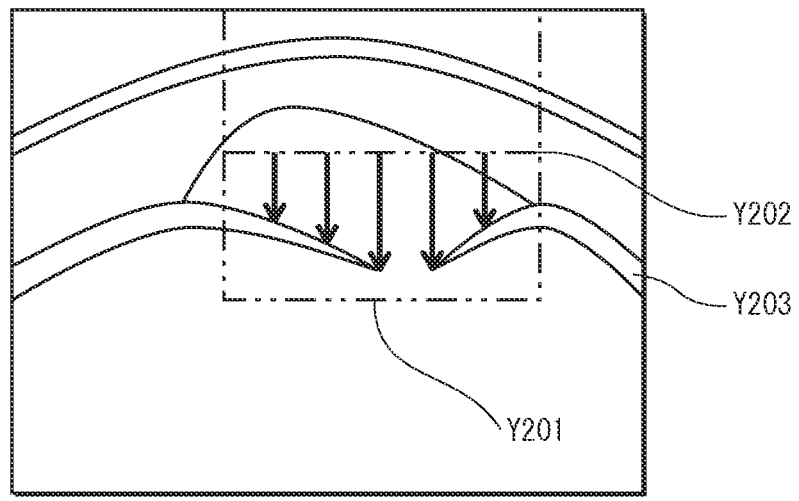
FIG. 21A illustrates an example of a bone cortex detection process.

FIG. 21A illustrates an example of a bone cortex detection process.

A joint detection window Y 201 is indicated. A reference line cuts through a vertical centre position Y 202 of the joint detection window Y 201. A bone Y 203 is extracted by the bone region extractor 13. A search range is defined as extending downward from the vertical centre position Y 202 of the joint detection window Y 201 (see the arrows in FIG. 21A). The search ends upon determining whether or not a high-luminance region has been reached, or upon determining whether or not edge strength and boundary smoothness reach a steady level according to a dynamic outline model (e.g., snake or similar).

Figure 21B:
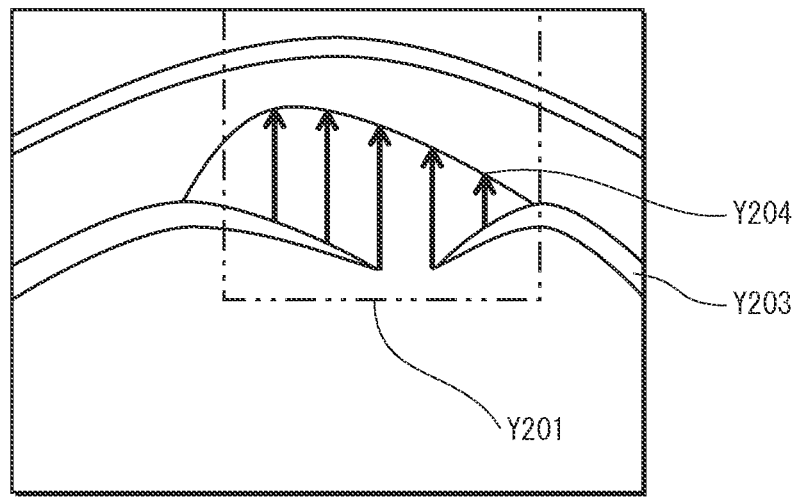
FIG. 21B illustrates an example of an articular capsule boundary detection process.

The articular capsule boundary detection operation by the joint detector 41 is described next. FIG. 21B illustrates an example of an articular capsule boundary detection process. An articular capsule boundary Y 204 is depicted. A search range extends upward from the bone Y 203 (see the arrows in FIG. 21A). As in the bone detection process, the search ends upon determining whether or not a high-luminance region has been reached, or upon determining whether or not edge strength and boundary smoothness reach a steady level according to a dynamic outline model (e.g., snake or similar). The size of the articular cavity is found by taking the area of the boundary between the bone Y 203 and the articular capsule Y 204. The luminance of the articular cavity is found by taking the average luminance of pixels between the bone Y 203 and the articular capsule Y 204. This concludes the description of the bone quality detection process and the articular cavity detection process by the joint detector 41.

(Swelling Score and Inflammation Score Calculation Operations)

The swelling score calculation operations performed by the shape quantifier 32 are described next. The swelling score GS is calculated according to a size of the articular cavity GSx, a luminance of the articular cavity GSy, and constants GSa and GSb.

$$GS = gsa \cdot GSx + gsb \cdot GSy \qquad \text{[Math. 1]}$$

The values of GSx and GSy may be regularised to have a range of zero to one, using the respective maxima and minima. This concludes the GS score calculation process performed by the shape quantifier 32.

Similarly, the inflammation quantifier 33 calculates the inflammation score (PD score) from the Doppler mode image. Specifically, the PD score is calculated using a Doppler signal area (PDx) located between boundaries of the bone Y 203 and the articular cavity Y 204, and a surface area (PDy) of the area between the boundaries of the bone Y 203 and the articular cavity Y 204. The PD score is calculated using Math. 2.

$$PD = PDx/PDy \qquad \text{[Math. 2]}$$

This concludes the PD score calculation process performed by the inflammation quantifier 33.

Once the swelling score and inflammation score has been calculated for the input image, the screen creator 27 creates the display screen using the swelling score and the inflammation score stored by the memory circuit 9. The operands of Math. 1 and Math. 2 include the area of the blood flow signal. When the vascular cross-section in the finger joint is small due to pressure from contact with the ultrasound probe, the blood flow speed changes and in turn, changes the value of PDx (the blood flow signal area) in Math. 2. Also, when the finger joint is under pressure from the ultrasound probe 102, the articular capsule is depressed, which changes the value of GSx in Math. 1 and of PDy in Math. 2. Thus, Embodiment 2 is able to exclude the Doppler mode image in which the articular cavity is under pressure from the ultrasound probe 102 from calculation of the swelling score and the inflammation score.

(Processing by the Ultrasound Diagnostic Device 101)

In conclusion to the explanation of Embodiment 2, the overall processing by the ultrasound diagnostic device pertaining to Embodiment 2 is described with reference to flowcharts. FIG. 22 illustrates an example of the overall processing by the ultrasound diagnostic device of Embodiment 2. In the flowchart, variable i represents a frame number of the frame subject to processing and serves as a control variable for loops in the process.

The flowchart of FIG. 22 begins with step S41, in which a determination is made regarding whether or not a measurement start operation has been made. In the affirmative case, the variable i is initialised in step S42, and the process makes a loop from step S43 through step S56. The loop process is as follows. First, the frame number i is displayed, and the frame position on the slide bar is updated to i (step S43). A processing message is then displayed (S44). Subsequently, the B-mode image and the Doppler mode image subject to measurement are displayed upon being obtained by transmitting and receiving the ultrasound (step S45).

Afterward, a determination is performed regarding whether or not the B-mode image and the Doppler mode image include a joint (step S46). In the affirmative case, steps S47 through S53 are performed. In the negative case, frame number i is excluded from quantifying in step S54, the value of i is incremented in step S55, and the loop returns to step S43.

Steps S47 through S53 are explained below. In step S47, a computation P=ma·Mx+mb·My+mz·Mz is performed, using an inter-frame displacement Mx, a Doppler signal area My, and a high-luminance Doppler region area Mz, taken from the Doppler mode image. Then, in step S48, a determination is made regarding whether the value of P is low, which indicates absence of motion noise. When the Doppler mode image having frame number i contains motion noise, then a display showing that frame number i is excluded from quantifying is made in step S54, the value of i is incremented in step S55, and the loop returns to step S43.

When no motion noise is present, the process of steps S49 through S53 is performed. In step S49, a determination is made regarding the positional relationship of the ultrasound probe. In step S50, the positional relationship is deemed appropriate or not appropriate. When the positional relationship is appropriate, the swelling score and the inflammation score for frame number i are calculated and displayed (step S51). Next, a determination is made regarding whether or not an end operation has been made (step S52), and regarding whether or not the value of i has reached the maximum frame number of 255 (step S53). When both determinations are affirmative, the process breaks out of the loop and returns. When both determinations are negative, the value of i is incremented in step S55 and the process returns to step S43. When only one of the determinations is affirmative, the process repeats steps S43 through S55.

Figure 23:
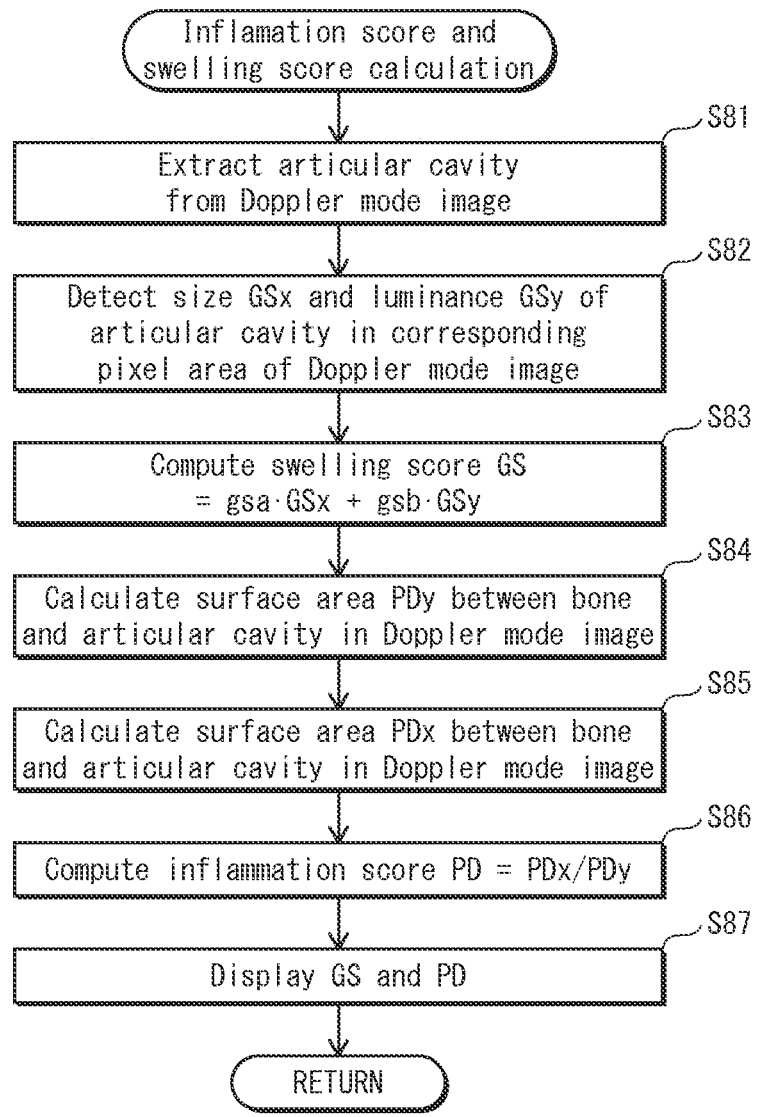
FIG. 23 illustrates an example of a calculation processes for a swelling score and an inflammation score.

In the above-described flowchart, the determination in step S49 regarding the positional relationship of the ultrasound probe and the calculations in step S51 regarding the swelling score and the inflammation score are performed as sub-routines each including more detailed processing. The flowchart of FIG. 11 illustrates the details of the positional relationship determination performed in step S49. FIG. 23 illustrates the details of the swelling score and inflammation score calculation operations.

FIG. 23 provides an example of the calculation processes for the swelling score and the inflammation score. The articular cavity is detected in the Doppler mode image (step S81). The size GSx and the luminance GSy of the articular cavity are detected in a pixel area corresponding to the articular cavity in the Doppler mode image (step S82). The swelling score GS is computed as GS=gsa·GSx+gsb·GSy (step S83). The area PDy between the bone and the articular cavity is calculated from the Doppler mode image (step S84). The area PDx between the bone and the articular cavity is calculated from the Doppler mode image (step S85). The inflammation score PD is computed as PD=PDx/PDy (step S86). The swelling score GS and the inflammation score PD are then displayed (step S87).

According to the above-described Embodiment, the degree of joint inflammation is calculated by excluding ultrasound images taken with non-appropriate technique from the evaluation process. A quantified degree of inflammation having low dependence on the operator enables quantifying a high probability of recurring inflammation.

(Supplement)

The best Embodiment of the disclosure known to the inventors at the time of application has been described above. However, further improvements and modifications are also possible, in terms of the following technical topics.

(Swelling Score and Inflammation Score)

When the swelling score and the inflammation score represent a degree of rheumatism symptoms, then no limitation to Math. 1 and Math. 2 is necessary.

(Positional Relationship Notification)

The aforementioned skin-probe distance calculator 17 is described as making a determination of whether or not the probe position is appropriate. However, this determination is not limited to a binary YES-NO representation, but may also be a numerical value indicating a degree of appropriateness (e.g., a percentile representation, a value from 0.0 to 1.0, or similar).

(Comparison to Threshold)

In FIGS. 11 and 12, determinations are made regarding whether or not the distance between the probe and the bone or skin satisfies a threshold at a predetermined number of pixels. This determination may also involve the distance being equal to or greater than a first threshold and equal to or shorter than a second threshold.

(Notification Method)

In Embodiments 1 and 2, the notification method for the positional relationship of the ultrasound probe 102 involves displaying a method, displaying a bar, or displaying a colour. However, other methods may also be used. For example, a sign may be used, or an illustration representing the positional relationship between the probe and the skin. Also, the appropriateness of the positional relationship between the ultrasound probe 102 and the body surface may be expressed by audio. For example, an alarm or buzzer may sound, or an audio announcement may be played back to explain that the positional relationship is not appropriate, such that the user is made aware that the positional relationship is not appropriate. Further, the user may be informed that the positional relationship is not appropriate by a blinking pilot lamp on the ultrasound probe 102.

(Ultrasound Diagnostic Device 101 Variations)

The ultrasound probe 102 and the display 103 may be internal components of the ultrasound diagnostic device 101. Also, some or all of the processing components of the ultrasound diagnostic device in each Embodiment may be included in the ultrasound probe 102.

(Frame Number Processing)

In Embodiment 2, the B-mode image and the Doppler mode image are displayed in association with one frame number. In such circumstances, the processing for a given frame (here, frame X) is beneficially performed as follows.

Frame X processing:
1) Acquire B-mode image for frame X
2) Determine presence of gel layer in B-mode image
3) When result of step 2 is affirmative, obtain Doppler mode image for frame X using predetermined Doppler window The Doppler window may be based on a representative distance from the skin surface to the articular cavity in an adult finger In other variations, the articular cavity is extracted from the B-mode image and the Doppler window is set within the articular cavity.

(Mode Setting for Articular Cavity Diagnostic)

In Embodiments 1 and 2, a notification regarding whether or not pressure is being applied to the body surface is beneficially issued when an articular cavity diagnostic mode setting is received and mode input is received for the articular cavity diagnostic mode. This approach enables a notification of whether or not the ultrasound probe is applying pressure to the body surface to be made only when the articular cavity is the diagnostic subject, thus reducing the frequency of notification.

(Diagnostic Subject)

In Embodiments 1 and 2, the diagnostic subject is new blood vessels within the articular cavity. However, no such limitation is intended. The disclosure may also be applied to cancer diagnostic. Specifically, the disclosure may be applied to detecting the presence of new blood vessels in a tumour during a cancer diagnostic.

(Ultrasound Probe 102 Variation)

The ultrasound probe 102 may have a one-dimensional array of ultrasound transducers, or may have a two-dimensional array block of ultrasound transducers arranged in a matrix. Also, the longitudinal edge of the ultrasound image has been described as corresponding to the element array of the ultrasound probe. However, the short-axis edge of the ultrasound image may also correspond to the element array of the ultrasound probe. When the acoustic element array direction of the ultrasound probe 102 pertaining to the Embodiments matches the short-axis direction of the ultrasound image. then the portion facing the acoustic element array is a portion surrounded by the ultrasound image short-axis and the skin outline.

(Integrated Circuit)

The components of the ultrasound diagnostic device pertaining to the Embodiments may be realised as an LSI, which is a type of integrated circuit. The components may each be realised on individual chips, or one or more components may be realised on a single chip. The integration method is not limited to LSI. A dedicated circuit or general-purpose processor may also be used. After LSI manufacture, a Field Programmable Gate Array (FPGA) or a reconfigurable processor may be used.

Also, the functions of the ultrasound diagnostic device pertaining to the Embodiments may be realised in whole or in part by a central processing unit (CPU), a graphics processing unit (GPU), a programmable device such as a processor, by software, or similar. The disclosure may also be realised as a program. The program may be recorded onto a non-transitory computer-readable recording medium. The program may also, of course, be transmitted through a transmission medium such as the Internet.

(Function Combination)

The functions of the ultrasound diagnostic device pertaining to the above-described Embodiments and Variations may be freely combined. Furthermore, the numerical values given above are intended only for describing a specific example of the disclosure, and do not represent any limitation to the given values.

(Function Blocks)

Division into functional blocks in the above-described block diagrams is intended only as example of functional blocks for realising a plurality of functions. Any of the functional blocks may be divided into further blocks, or a portion of one block may be moved to another block. Also, parallel or time-division processing may be performed by hardware or by software to perform a plurality of similar functions at once.

(Step Ordering)

The ordering of the above-described steps is intended only as a specific example for describing the disclosure. Other orderings are also possible. A subset of the above-described steps may be performed simultaneously (i.e., in parallel) with other steps. Further Variations considered by those skilled in the art may also be applied provided that these do not exceed the main scope of the Embodiments.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound diagnostic device, comprising:
a transceiver circuit causing an ultrasound probe to transmit and receive an ultrasound;
an image generation circuit generating an ultrasound image according to the ultrasound received by the ultrasound probe; and
a control circuit, wherein
the ultrasound image is a cross-section that includes a measurement target, and
the control circuit executes:
a region determination of determining one of a presence and a thickness of a pixel region having a luminance distribution specific to gelatinous material, within a portion of the ultrasound image opposite an element array of the ultrasound probe; and a positional relationship notification of making a notification to a user regarding whether or not there is an appropriate positional relationship between the measurement target and the ultrasound probe, according to the one of the presence and the thickness of the pixel region.

2. The ultrasound diagnostic device of claim 1, wherein the pixel region having the luminance distribution specific to gelatinous material is made up of pixels having low luminance relative to the measurement target.

3. The ultrasound diagnostic device of claim 1, wherein the pixel region having the luminance distribution specific to gelatinous material is made up of pixels having uniform luminance.

4. The ultrasound diagnostic device of claim 3, wherein a determination of uniform luminance is made by calculating an evaluation score for evaluating uniformity of the portion of the ultrasound image opposite the element array of the ultrasound probe, based on a luminance distribution and an average luminance, and determining whether or not the evaluation score is within a predetermined numerical range.

5. The ultrasound diagnostic device of claim 1, wherein the region determination further involves extracting a predetermined area that is characteristic of the measurement target from the ultrasound image, and
the pixel region having the luminance distribution specific to gelatinous material ranges from the portion of the ultrasound image opposite the element array of the ultrasound probe to the predetermined area.

6. The ultrasound diagnostic device of claim 5, wherein the predetermined area is one of a bone region and a skin region, and is made up of pixels having high luminance relative to a surrounding area within the ultrasound image.

7. The ultrasound diagnostic device of claim 5, wherein the region determination further involves extracting a contour line of the portion of the ultrasound image opposite the element array of the ultrasound probe, and
the predetermined area is one of a bone region and a skin region, defined by the contour line.

8. The ultrasound diagnostic device of claim 7, wherein a template of a bone region and a skin region is registered in advance,
the region determination further involves pattern matching of a plurality of local regions within the ultrasound image to the template, and selecting one of the local regions as matching one of the bone region and the skin region according to a matching result, and
the predetermined area is one of the bone region and the skin region, as selected among the local regions.

9. The ultrasound diagnostic device of claim 7, wherein an identifier for distinguishing a bone region and a skin region obtained by machine learning is registered in advance, and
the region determination further involves applying the identifier to a plurality of local regions within the ultrasound image, and distinguishing one of the bone region and the skin region.

10. The ultrasound diagnostic device of claim 1, further comprising
a display output circuit causing a message to be displayed with the ultrasound image on a display screen of a display device, wherein
the positional relationship notification further involves changing the message according to the positional relationship of the probe.

11. The ultrasound diagnostic device of claim 1, further comprising
a display output circuit causing a bar graph to be displayed with the ultrasound image on a display screen of a display device, wherein
the positional relationship notification further involves changing a position on the bar graph according to the positional relationship of the probe.

12. The ultrasound diagnostic device of claim 1, further comprising
a display output circuit causing the ultrasound image to be displayed on a display screen of a display device, wherein
the positional relationship notification further involves changing a colour of a portion of the display screen according to the positional relationship of the probe.

13. The ultrasound diagnostic device of claim 1, wherein the ultrasound probe acquires a frame image sequence by transmitting and receiving the ultrasound to a plurality of positions of the measurement target,
the ultrasound image is one among a plurality of frame images within the frame image sequence,
the region determination is performed for the pixel region having the luminance distribution specific to gelatinous material in each of the frame images,
the control circuit executes a quantification determination and a disease progression score calculation,
the quantification determination involves determining whether or not each of the frames should be excluded from the quantification, according to a respective determination result for each of the frames,
the disease progression score calculation involves calculating a disease progression score indicating progression of swelling or inflammation in the measurement target for all frame images not excluded from the quantification, and
the positional relationship notification includes displaying, on a display device, the notification regarding the positional relationship between the ultrasound probe and the measurement target in association with the disease progression score.

* * * * *